US008889389B2

(12) United States Patent
Kosugi et al.

(10) Patent No.: US 8,889,389 B2
(45) Date of Patent: *Nov. 18, 2014

(54) PROCESS FOR PRODUCING PROTEIN A-LIKE PROTEIN WITH USE OF BREVIBACILLUS GENUS BACTERIUM

(71) Applicant: Kaneka Corporation, Osaka (JP)

(72) Inventors: Akihiko Kosugi, Tsukuba (JP); Kazuyoshi Yajima, Akashi (JP)

(73) Assignee: Kaneka Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,231

(22) Filed: Oct. 29, 2013

(65) Prior Publication Data
US 2014/0080179 A1 Mar. 20, 2014

Related U.S. Application Data

(62) Division of application No. 11/630,334, filed as application No. PCT/JP2005/012252 on Jul. 1, 2005, now Pat. No. 8,597,908.

(30) Foreign Application Priority Data

Jul. 6, 2004 (JP) ................. 2004-198831

(51) Int. Cl.
C12P 21/06 (2006.01)
C12N 11/14 (2006.01)
C12N 15/00 (2006.01)
C12N 1/20 (2006.01)
C12P 21/02 (2006.01)
C07K 16/12 (2006.01)
C07K 14/31 (2006.01)

(52) U.S. Cl.
CPC ............. C07K 16/1271 (2013.01); C12P 21/02 (2013.01); C07K 14/31 (2013.01)
USPC .... 435/176; 435/69.1; 435/252.3; 435/320.1; 536/23.1

(58) Field of Classification Search
USPC .................... 435/69.1, 252.3, 320.1; 536/23.1
See application file for complete search history.

(56) References Cited

U.S. PATENT DOCUMENTS

| 4,617,266 | A | 10/1986 | Fahnestock |
| 5,151,350 | A | 9/1992 | Colbert et al. |
| 5,260,373 | A | 11/1993 | Profy et al. |
| 5,665,570 | A | 9/1997 | Yamagata et al. |
| 5,714,346 | A | 2/1998 | Udaka et al. |
| 7,655,452 | B1 | 2/2010 | Hanagata et al. |

FOREIGN PATENT DOCUMENTS

| EP | 0107509 A2 | 5/1984 |
| EP | 0124374 A1 | 11/1984 |
| EP | 0257189 | 3/1988 |
| EP | 0 667 394 A2 | 8/1995 |
| EP | 0 741 189 A1 | 11/1996 |
| EP | 1270730 A2 | 1/2003 |
| JP | 59113890 A | 6/1984 |
| JP | 59205996 A | 6/1984 |
| JP | 6058074 A | 4/1985 |
| JP | 62111688 A | 5/1987 |
| JP | 63503032 T | 11/1988 |
| JP | 3251185 A | 11/1991 |
| JP | 2004-278091 A | 10/1992 |
| JP | 04278091 A | 10/1992 |
| JP | 4278091 A | 10/1992 |
| JP | 5051399 A | 3/1993 |
| JP | 5328970 A | 12/1993 |
| JP | 6038741 A | 2/1994 |
| JP | 6253883 A | 9/1994 |
| JP | 06296485 | 10/1994 |
| JP | 6296485 A | 10/1994 |
| JP | 751072 A | 2/1995 |
| JP | 7059580 A | 3/1995 |
| JP | 7107980 A | 4/1995 |
| JP | 7184642 A | 7/1995 |
| JP | 07265094 | 10/1995 |
| JP | 7265094 A | 10/1995 |
| JP | 8107795 A | 4/1996 |
| JP | 10218895 A | 8/1998 |
| JP | 10225294 A | 8/1998 |
| JP | 11178574 A | 7/1999 |
| JP | 2000-500649 A | 1/2000 |
| JP | 2001078771 A | 3/2001 |
| JP | 2003079379 A | 3/2003 |

(Continued)

OTHER PUBLICATIONS

European Search Report for EP Application No. 05755845.4 dated Feb. 25, 2008.
Stephen R. Fahnestock, et al., "Expression of the Staphylococcal Protein A Gene in Bacillus subtilis by Gene Fusions Utilizing the Promoter from a Bacillus amyloliquefaciens alpha-Amylase Gene", Journal of Bacteriology, 1986, 165(3): 796-804.
Shigezo Udaka, et al., "High-Level Secretion of Heterologous Proteins by Bacillus bevis", Methods in Enzymology, 1993, 217: 23-33.
A. Miyauchi, et al., "Pilot scale production of a recombinant human epidermal growth factor, secreted by Bacillus brevis, using expanded bed adsorption", Journal of Industrial Microbiology & Biotechnology, 1998, 21: 208-214.

(Continued)

Primary Examiner — Maryam Monshipouri
(74) Attorney, Agent, or Firm — Sughrue Mion, PLLC

(57) ABSTRACT

The present invention relates to an efficient and economical process for producing a protein A-like protein. Hosts such as Escherichia coli and Bacillus subtilis have been used in the production of a protein A-like protein using a genetic recombination technique and however, their low productivity has been a big cause of high cost. Thus, it has been desired strongly to immediately establish a technique enabling the inexpensive, large-scale production of a protein A-like protein using recombinant DNA techniques other than Escherichia coli and Bacillus subtilis. The present invention provides a process for producing a protein A-like protein in large amounts, for example, a process comprising allowing a recombinant Brevibacillus genus bacterium to express and secrete the protein in large amounts into a culture solution and separating and collecting the accumulated protein A-like protein from the culture solution.

8 Claims, 9 Drawing Sheets

(56) References Cited

FOREIGN PATENT DOCUMENTS

| | | |
|---|---|---|
| JP | 2003135060 A | 5/2003 |
| JP | 2003135068 A | 5/2003 |
| JP | 2003169675 A | 6/2003 |
| JP | 2004129576 A | 4/2004 |
| JP | 2005-538693 A | 12/2005 |
| WO | 87/05631 A1 | 9/1987 |
| WO | 98/22598 A1 | 5/1998 |
| WO | 2005/045005 A1 | 5/2005 |

OTHER PUBLICATIONS

Makoto Takao, et al., "Production of swine pepsinogen by protein-producing *Bacillus brevis* carrying swine pepsinogen cDNA", Applied Microbiology and Biotechnology, 1989, 30: 75-80.

Norihiro Tsukagoshi, et al., "Molecular Cloning of a Major Cell Wall Protein Gene from Protein-Producing *Bacillus brevis* 47 and Its Expression in *Escherichia coli* and *Bacillus subtilis*", Journal of Bacteriology, 1984, 158(3): 1054-1060.

Stephen R. Fahnestock, et al., "Expression of teh Staphylococcal Protein A Gene in *Bacillus subtilis* by Integration of the Intact Gene into the *B. subtilis* Chromosome", Journal of Bacteriology, 1986, 165(3): 1011-1014.

Marjo Simonen, et al., "Protein Secretion in *Bacillus* Species", Microbiological Reviews, 1993, 57(1): 109-137.

Juzo Udaka, et al., "Technique for production of heterologous protein", Bio Industry, CMC Publishing Co., Ltd., 1992, 9(2): 23-31.

European Office Action issued in EP 05755845.4, dated Aug. 21, 2008.

Y. Inoue et al., "Efficient production of a functional mouse/human chimeric Fab' against human urokinase-type plasminogen activator by *Bacillus brevis*", Appl. Microbiol. Biotechnol., 1997, 48:487-492.

SG Invitation to Respond to Written Opinion, dated Jul. 10, 2009, issued in corresponding Singapore Application No. 200608966-8, 7 pages.

Japanese Office Action issued Dec. 15, 2009, in JP 2006-528867.

Summons to Attend Oral Proceedings issued Mar. 18, 2010, in EP 05755845.4.

Mi-Na Kweon et al., A Nontoxic Chimeric Enterotoxin Adjuvant Induces Protective Immunity in Both Mucosal and Systemic Compartments with Reduced IgE Antibodies, The Journal of Infectious Diseases, 2002, 186: 1261-1269.

Y. Yokomizo et al., "Mucosal immunoadjuvant activity of the low toxic recombinant *Escherichia coli* heat-labile enterotoxin produced by *Bacillus brevis* for the bacterial subunit or component vaccine in pigs and cattle", Veterinary Immunology and Immunopathology, 2002, 87: 291-300.

Japanese Office Action issued Feb. 22, 2010, in JP 2006-528867.

Hiroaki Takagi et al., "Characterization of *Bacillus brevis* with Descriptions of *Bacillus migulanus* sp. nov., *Bacillus choshinensis* sp. nov., *Bacillus parabrevis* sp. nov., and *Bacillus galactophilus* sp. nov.", International Journal of Systematic Bacteriology, 1993, 43(2): 221-231.

Explanation on th ebacterium of genus *Brevibacillus* on Website of Incorporated Administration Agency National Institute of Technology and Evaluation, http://www.bio.nite.go.jp/ngac/brevis.html, 2010.

*Brevibacillus brevis* Catalogue Detail Information from the National Institute of Technology and Evaluation, http://www.nbrc.nite.go.jp/NBRC2/NBRCCatalogueDetailServlet?ID=NBRC&CAT=00015304, 2010.

*Brevibacillus choshinensis* Catalogue Detail Information from the National Institute of Technology and Evaluation, http://www.nbrc.nite.go.jp/NBRC2/NBRCCatalogueDetailServlet?ID=NBRC&CAT=00015518, 2010.

Hiroaki Takagi et al., "Development of the Industrial Production of a Recombinant Epidermal Growth Factor, Secreted by *Bacillus brevis*", Nippon Nogeikagaku Kaishi, 2000, 74(1): 9-17.

Norihiro Tsukagoshi (Ed.), Seibutsu-Kagaku-Jikkenhou 45: Kumikaetanpakusitsu-Seisanhou (Biochemical experimental method 45: Production method of recombinant protein), Japan Scientific Societies Press, Tokyo, May 15, 2001, pp. 39-54.

Shigezo Udaka, "Discovery of Hyper Protein-Producing Bacteria and Their Utilization to the Production of Useful Proteins", Nippon Nogeikagaku Kaishi, 1987, 61(6): 669-676.

Osamu Shida, "Proposal for Two New Genera, *Brevibacillus* gen. nov. and *Aneurinibacillus* gen. nov.", International Journal of Systematic Bacteriology, vol. 46, No. 4, Oct. 1996, pp. 939-946.

Mathias Uhlen, et al., "Complete Sequence of the Staphylococcal Gene Encoding Protein A. A Gene Evolved Through Multiple Duplications", The Journal of Biological Chemistry, vol. 259, No. 3, Feb. 10, 1984 pp. 1695-1702.

Sven Loefdahl, et al., "Gene for Staphylococcal Protein A", Proceedings of the National Academy of Sciences of the United States of America, vol. 80, No. 3, Feb. 1983, pp. 697-701.

Nagao et al., "Secretory Production of Erythropoietin and the Extracellular Domain of the Erythropoietin Receptor by *Bacillus brevis*: Affinity Purification and Characterization", Biosci. Biotech. Biochem., 1997, 61(4):670-674.

Takagi et al., "Gene Expression in *Bacillus brevis* under Control of the Lac Repressor-Operator System from *Escherichia coli*", Journal of Fermentation and Bioengineering, 1992, 74(1):1-6.

PROCESS FOR PRODUCING PROTEIN A-LIKE PROTEIN WITH USE OF BREVIBACILLUS GENUS BACTERIUM

This is a Divisional Application of U.S. application Ser. No. 11/630,334 filed on Dec. 21, 2006, now U.S. Pat. No. 8,597,908, which is a National Phase Application of PCT application PCT/JP2005/012252 filed on Jul. 1, 2005, claiming priority based on Japanese Application No. JP 2004-198831 filed on Jul. 6, 2004, the contents of which are incorporated herein by reference in their entirety.

TECHNICAL FIELD

The present invention relates to a process for producing a protein A-like protein having immunoglobulin-binding ability with use of a *Brevibacillus* genus bacterium. Specifically, the present invention relates to the hyper expression and secretion of a protein A-like protein by a *Brevibacillus* genus bacterium by using a genetic recombination technique, to the separation and collection of the expressed protein A-like protein at high purity without undergoing degradation by protease and the like, and to the effective use of the separated and collected protein A-like protein in applications such as a column resin for antibody purification.

CROSS REFERENCE TO RELATED APPLICATION

All the disclosed contents including the specification, claims, drawings, and summary of Japanese Patent Application No. 2004-198831 (applied on Jul. 6, 2004) are incorporated to the present application by reference in their entirety.

BACKGROUND ART

Antibody (immunoglobulin, or also called Ig) proteins have been utilized as pharmaceutical drugs since long ago because of having the function of capturing and eliminating antigens harmful to organisms. Progress in genetic engineering techniques and cell fusion techniques in recent years made it possible to produce monoclonal antibodies that are more homogeneous and have high antigenicity by molecularly designing antibodies that react with their specific antigens and expressing the antibodies in animal cells. These antibody proteins are secreted into cell culture solutions and as such, can be separated, purified, and collected with relative ease.

In general, antibody proteins utilized in immunoassay or immunoblot analysis can be obtained at sufficient yields and purity from natural biological samples such as serum, ascites, or cell culture solutions by using a method utilized in usual protein purification, that is, an ammonium sulfate precipitation method, ion-exchange chromatography, and so on.

On the other hand, separation and purification using these methods for antibody proteins utilized in pharmaceutical drugs or diagnostic drugs or the like, which require high purity, involve contemplating various separation/extraction conditions and using a large number of other chromatography techniques together therewith and also involve optimizing purification conditions for each antibody protein, resulting in a great deal of time and labor. Thus, in the purification of antibody proteins required to be highly pure, affinity chromatography capable of specifically adsorbing the antibody proteins is generally used for conveniently separating and purifying them from other impurities.

Chromatography using a medium comprising an appropriate resin immobilizing thereon proteins such as protein A, protein G, and protein L is utilized most frequently as affinity chromatography having antibody-binding ability. Among these proteins, particularly the protein A is often utilized as a ligand on a medium for purification. The protein A is one kind of cell wall protein with a reported molecular weight of approximately 42,000 produced by a Gram-positive bacterium *Staphylococcus aureus*. Its structure is composed of seven functional domains (from the amino terminus, signal sequence S, immunoglobulin-binding domain E, immunoglobulin-binding domain D, immunoglobulin-binding domain A, immunoglobulin-binding domain B, immunoglobulin-binding domain C, and *Staphylococcus aureus* cell wall-binding domain X) (see Non-Patent Documents 1, 2, and 3). These five immunoglobulin-binding domains (domains E, D, A, B, and C) of the protein A can respectively bind to immunoglobulin through its Fc region (see Non-Patent Document 3).

The relative affinity of this protein A for the immunoglobulin-binding domains has been known to depend on many factors such as pH, the types of *Staphylococcus aureus* strains (Cheung, A. et al., Infec. Immun. 1987. 55: 843-847), and immunoglobulin class (IgG, IgM, IgA, IgD, and IgE) and subclass (IgG1, IgG2, IgG3, IgG4, IgA1, and IgA2), and these domains particularly show strong binding to the Fc region of human IgG1, IgG2, and IgG4, and mouse IgG2a, IgG2b, and IgG3 among immunoglobulin class. The protein A having these properties can bind to immunoglobulin without impairing antigen-binding ability, affinity, and properties as immunoglobulin, and as such, has been used widely as a ligand on a medium for purification of immunoglobulin, particularly IgG, used in various diagnoses, pharmaceutical drugs, and basic researches.

Alternatively, interest has recently been directed toward its application to such cancer therapy that serum blocking factors (composed of specific antigens, antibodies, anti-globulins, and immune complexes), which inhibit the cytotoxicity of sensitized peripheral blood lymphocytes to tumor cells, are adsorbed to protein A and thereby removed from the serum of a patient with tumor (see Patent Documents 1 to 3). Furthermore, protein A has, in addition to IgG-binding activity, the action of activating polyclonal antibody synthesis and has therefore been expected to be used for not only the initial application as a purification resin ligand but also various applications in biotechnology fields.

In an initial process for producing protein A, its separation and purification have been performed directly from the culture solution of *Staphylococcus aureus* strains. However, due to the problem on the pathogenicity of this bacterium or the contamination by impurities, the process is now shifting toward a producing process that uses a recombinant DNA technique using *Escherichia coli* (Patent Documents 1 to 3) or a Gram-positive bacterium *Bacillus subtilis* (Patent Documents 4 to 5). However, the recombinant protein A productivity of *Escherichia coli* is extremely low, and proteins expressed are not easy to separate and collect because most of them form inclusion bodies or are intracellularly degraded (Non-Patent Document 4). On the other hand, protein A production using *Bacillus subtilis*, a Gram-positive bacterium, as with *Staphylococcus aureus*, has adopted a method wherein protein A is secreted and expressed into a medium by adding the signal sequence of a *Bacillus subtilis* secreted protein to the N-terminus of protein A. This method, when compared with the production system with *Escherichia coli*, has been reported to provide easy separation and purification and have high productivity (approximately 47 to 100 mg/L) (Fahnestock, S, R. et al., J. Bacteriol. 1986. 165: 796-804). However, the protein A produced in *Bacillus subtilis* undergoes degradation by extracellular protease intrinsically carried by *Bacillus subtilis*. Therefore, attempts have been made to use several kinds of extracellular protease-deficient *Bacillus subtilis* strains (Non-Patent Document 5) as hosts. However, the inhibition of degradation of protein A has not been achieved yet.

[Patent Document 1] Japanese Patent Application No. 07-187019
[Patent Document 2] U.S. Pat. No. 5,151,350
[Patent Document 3] European Patent No. EP0107509
[Patent Document 4] U.S. Pat. No. 4,617,266
[Patent Document 5] European Patent No. EP0124374
[Non-Patent Document 1] Lofdahl, S et al., Proc. Natl. Acad. Sci. USA. 1983. 80: 697-701.
[Non-Patent Document 2] Shuttleworth, H. L et al., Gene. 1987. 58: 283-295.
[Non-Patent Document 3] Uhlen, M. et al., J. Bio. Chem. 1984. 259: 1695-1702.
[Non-Patent Document 4] Nilsson, B et al., Protein Eng. 1987. 1: 107-113.
[Non-Patent Document 5] Fahnestock, S. R et al., Appl. Environ. Microbiol. 1987. 53: 379-384.
[Non-Patent Document 6] Brigido, M et al., J. Basic Microbiology. 1991. 31: 337-345.
[Non-Patent Document 7] Sjostrom, J, -E et al., J. bacteriol. 1975. 123: 905-915.
[Non-Patent Document 8] Bjorck, L. et al., 1984. J. Immunol. 133, 969-974.
[Non-Patent Document 9] Kastern, W. et al., J Biol. Chem. 1992. 267: 12820-12825
[Non-Patent Document 10] Udaka, S. et al., Method Enzymol. 1993. 217: 23-33.

DISCLOSURE OF THE INVENTION

Problems to be Solved by the Invention

Against this backdrop, it has been demanded strongly to establish a more efficient protein A production technique than the producing process using *Escherichia coli* or *Bacillus subtilis*.

An object of the present invention is to provide a more efficient protein A production technique than the producing process using *Escherichia coli* or *Bacillus subtilis*.

Means for Solving the Problems

To establish a stable, large-scale production technique for functional proteins such as protein A, the present inventors have conducted diligent studies with a *Brevibacillus* genus bacterium as a host and consequently found that protein A can be secreted and expressed efficiently in large amounts into a culture solution, allowed to stably accumulate therein, and separated and collected easily at high purity.

Advantages of the Invention

According to the present invention, protein A can be produced and secreted, into a culture solution, with drastically exceeding yields than those reported on microorganisms such as *Escherichia coli* and *Bacillus subtilis* used as hosts, by using a *Brevibacillus* genus bacterium as a host, and can be purified easily at high purity without impairing its immunoglobulin-binding function. Thus, the present invention solves low productivity and complicated purification steps for protein A, which have been a cause of high cost so far.

The present invention comprises the following one or several aspects:

(1) The present invention provides a DNA sequence comprising a DNA sequence encoding a protein A-like protein or partial sequence thereof, and a promoter which is operatively linked to the sequence and is capable of functioning in a *Brevibacillus* genus bacterium.
(3) The present invention provides an expression vector comprising the DNA sequence.
(4) The present invention provides a *Brevibacillus* genus bacterium transformant comprising the expression vector.
(6) The present invention provides a process for producing a protein A-like protein or protein having a partial sequence thereof, comprising culturing the transformant and collecting a protein A-like protein or a protein having a partial sequence thereof produced and secreted by the transformant.
(7) The present invention provides a process for producing an immunoglobulin-adsorbing medium, comprising producing a protein A-like protein or protein having a partial sequence thereof by the producing process and immobilizing the protein-like protein or protein having a partial sequence thereof onto an appropriate base matrix.

BRIEF DESCRIPTION OF THE DRAWINGS

FIG. 1 is a diagram showing the nucleotide sequence and amino acid sequence of the protein A of a *Staphylococcus aureus* Cowan I strain (numerals represent amino acid residue numbers);

FIG. 2 is a diagram showing the gene sequence and amino acid sequence of the protein A of a *Staphylococcus aureus* strain (numerals represent amino acid residue numbers);

BEST MODE FOR CARRYING OUT THE INVENTION

Figure 3:
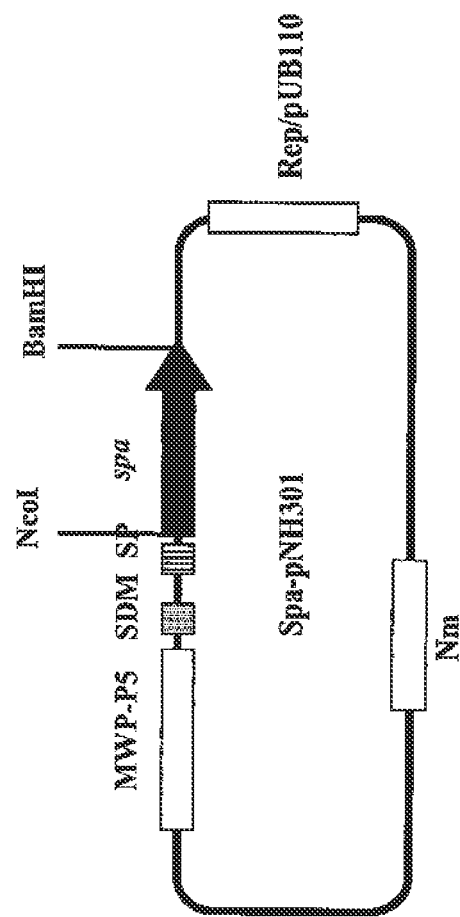
FIG. 3 is a diagram showing protein A (SPA) expression vector (Spa-pNH301)

The present inventors have found that active protein A can be expressed and secreted in large amounts into a culture solution by using a Gram-positive *Brevibacillus* genus bacterium among bacteria to which a recombinant DNA technique can be applied, and as a result, the problem of low productivity of *Escherichia coli* and *Bacillus subtilis* as well as the problem of degradation of protein A expressed in *Bacillus subtilis* is effectively improved. Specifically, the use of the *Brevibacillus* genus bacterium can easily secure a protein A expression level equal to that obtained in *Bacillus subtilis* and further accumulate it into a medium. Hereinafter, the present invention will be described in detail on the basis of its embodiments.

1. Protein A

Figure 1:
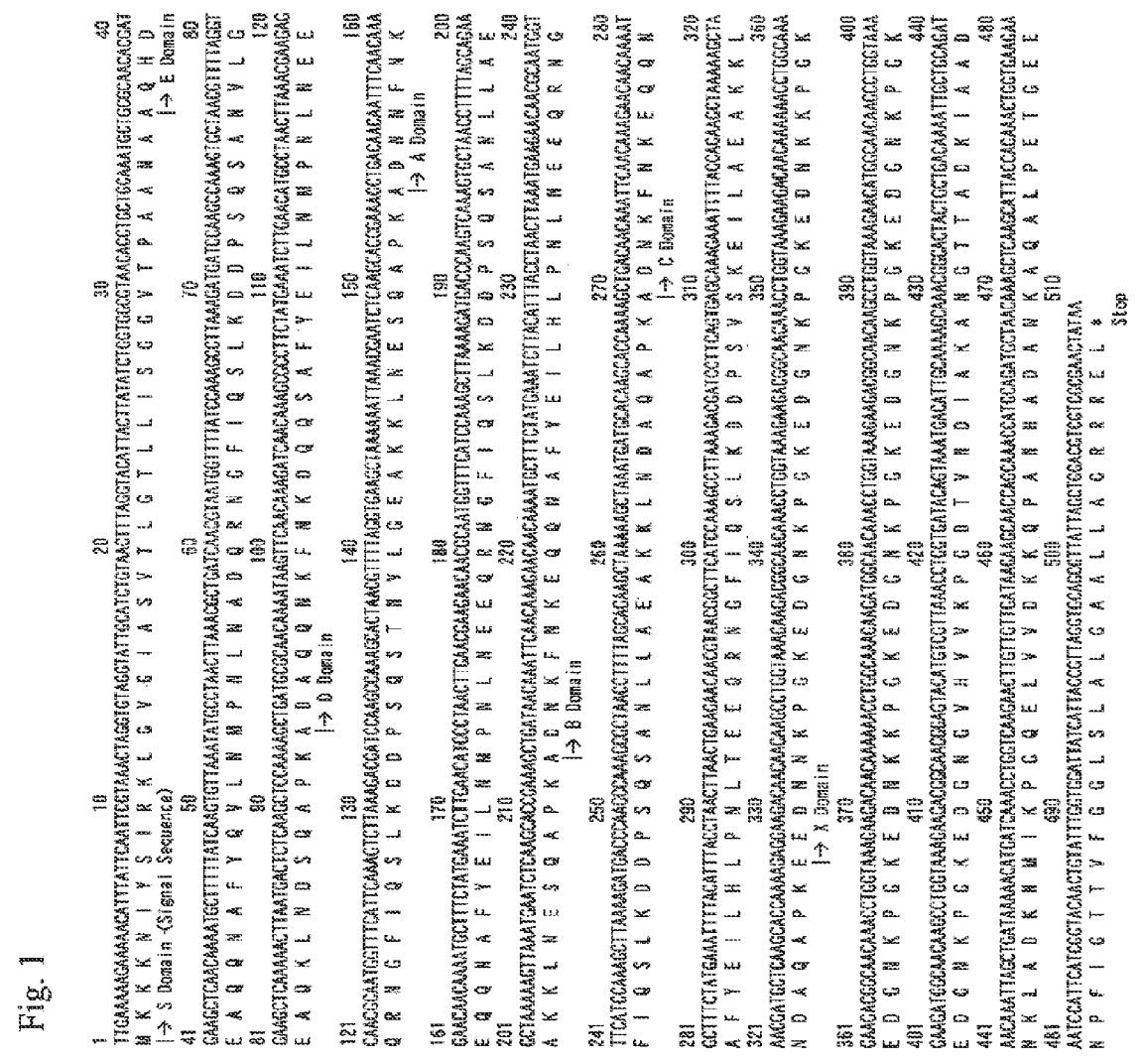
Figure 2:
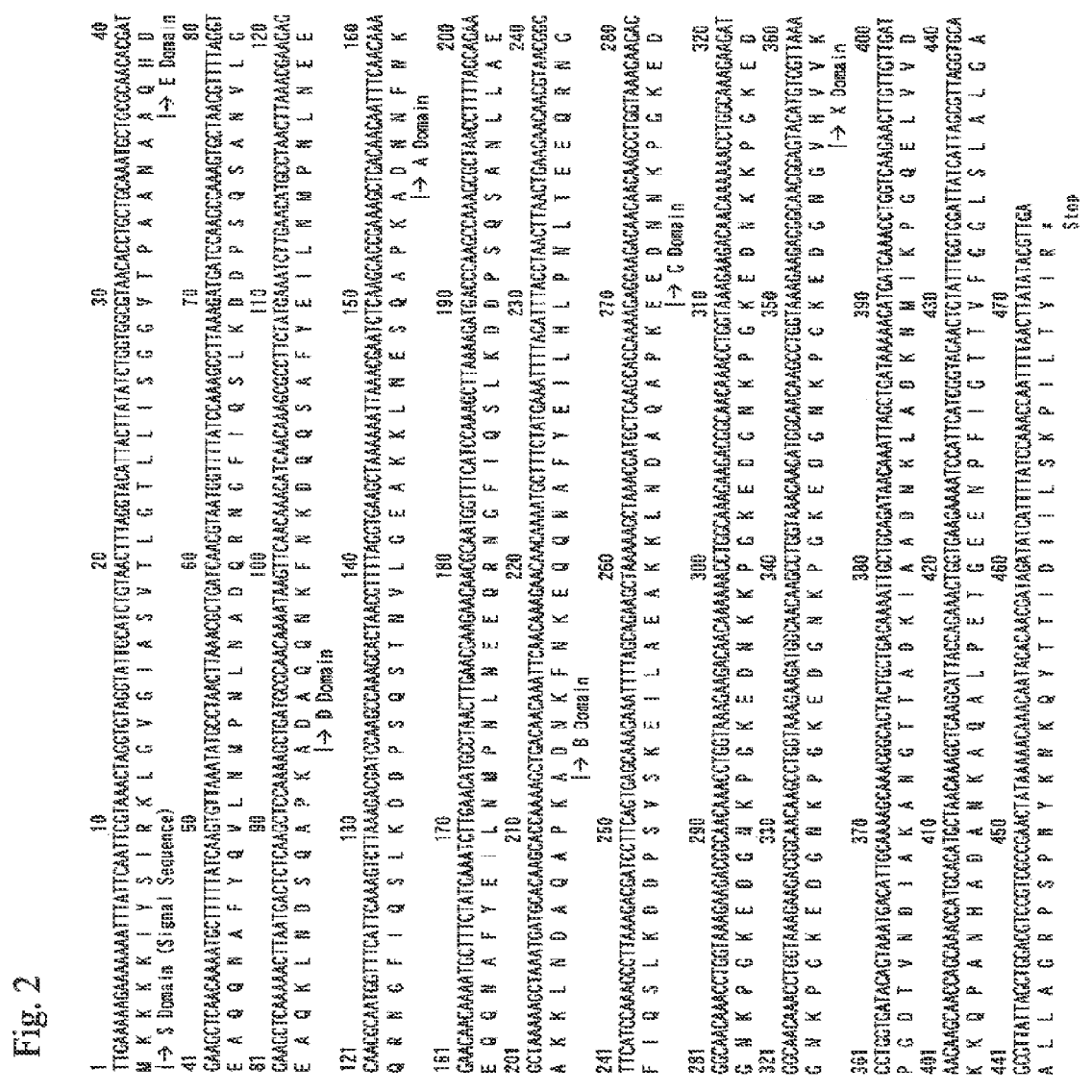

Protein A, as described above, is one kind of cell wall protein produced by a Gram-positive bacterium *Staphylococcus aureus* and refers to, for example, one consisting of the amino acid sequence represented by FIG. 1 (SEQ ID NO: 2) and derived from a *Staphylococcus aureus* Cowan I strain (JCM2179) (Non-Patent Document 2), one consisting of the amino acid sequence represented by FIG. 2 (SEQ ID NO: 4) (Non-Patent Document 6; and Finck-Barbancon, V. et al., FEMS Microbiol. Lett. 1992. 91: 1-8), one derived from a Woods 46 strain (Non-Patent Document 3), one derived from a 8325-4 strain (Non-Patent Document 3), and spa gene products encoded by already cloned plasmid DNA (i.e., pSP1, pSP3, etc., (Non-Patent Document 7)).

A protein A-like protein described in the present invention includes protein A or a protein substantially identical to protein A. The protein A-like protein also includes a protein that has an amino acid sequence having at least 60%, preferably 80%, more preferably 90 to 95%, most preferably at least 99% amino acid residue identity in comparison with the amino acid sequence of protein A when the sequence is aligned with the amino acid sequence of protein A for the best match using sequence comparison algorithm generally known by those skilled in the art, and has immunoglobulin-binding activity. In this context, the amino acid sequence having identity is preferably 50 or more residues, more preferably 100 or more residues, even more preferably 150 or more residues in length, and in the most preferable embodiment, the full-length amino acid sequence has identity thereto.

An example of algorithm suitable for determining % sequence identity is BLAST algorithm, and this algorithm has been described in Altschul et al., J. Mol. Biol. 215: 403-410 (1990). Software for implementing BLAST analysis is publicly available through National Center for Biotechnology Information (www.ncbi.nlm.nih.gov/).

The protein A-like protein may be, for example, a protein consisting of an amino acid sequence encoded by DNA hybridizing under stringent conditions to DNA having a sequence complementary to the DNA sequence represented by SEQ ID NO: 1 or 3. An example of hybridization conditions under the stringent conditions is: preferably, hybridization at approximately 50° C. in approximately 7% sodium dodecyl sulfate (SDS), approximately 0.5 M $NaPO_4$, and 1 mM EDTA, and washing at 50° C. in approximately 2×SSC and approximately 0.1% SDS; more desirably, hybridization at 50° C. in approximately 7% sodium dodecyl sulfate (SDS), approximately 0.5 M $NaPO_4$, and approximately 1 mM EDTA, and washing at approximately 50° C. in approximately 1×SSC and approximately 0.1% SDS; more desirably, hybridization at approximately 50° C. in approximately 7% sodium dodecyl sulfate (SDS), approximately 0.5 M $NaPO_4$, and approximately 1 mM EDTA, and washing at approximately 50° C. in approximately 0.5×SSC and approximately 0.1% SDS; more preferably, hybridization at approximately 50° C. in approximately 7% sodium dodecyl sulfate (SDS), approximately 0.5 M $NaPO_4$, and approximately 1 mM EDTA, and washing at approximately 50° C. in approximately 0.1×SSC and approximately 0.1% SDS; and even more preferably, at approximately 50° C. in approximately 7% sodium dodecyl sulfate (SDS), approximately 0.5 M $NaPO_4$, and approximately 1 mM EDTA, washing at approximately 65° C. in approximately 0.1×SSC and approximately 0.1% SDS. The conditions, of course, may differ depending on a nucleotide strand length, the sequence, and different environmental parameters. A longer sequence specifically hybridizes at a higher temperature. A detailed guide for nucleic acid hybridization is found in, for example, Tijssen (1993) Laboratory Techniques in Biochemistry and Molecular Biology—Hybridization with Nucleic Acid Probes part I chapter 2 "Overview of principles of hybridization and the strategy of nucleic acid probe assay" Elsevier, New York.

As described above, those skilled in the art of genetic engineering can easily recognize the presence of the "protein A-like protein" and the DNA sequence encoding it by knowing the protein A-encoding DNA sequences and protein A amino acid sequences represented by FIG. 1 (SEQ ID NOs: 1 and 2) and FIG. 2 (SEQ ID NOs: 3 and 4).

The "protein A-like protein" also includes, for example, those comprising protein A-constituting immunoglobulin-binding domains (E, D, A, B, and C) rearranged in an arbitrary order.

Furthermore, "the protein A-like protein" also includes, for example, proteins having immunoglobulin-binding function analogous to that of protein A such as protein G carried by group C and G Streptococcal bacteria (Non-Patent Document 8) or protein L from *Peptostreptococcus magnus* (Non-Patent Document 9).

2. Partial Sequence of Protein A-Like Protein

A "partial sequence" of the protein A-like protein refers to a protein that is composed of an arbitrary portion of the amino acid sequence constituting the protein A-like protein and has immunoglobulin-binding activity. Specifically, the "partial sequence" of the protein A-like protein corresponds to, for example, each of an amino acid sequence represented by the 24th Ala and the subsequent sequence in SEQ ID NO: 8 (corresponding to "SPA" of Example 1; see FIGS. 3 and 4 and SEQ ID NOs: 7 and 8), which is obtained by removing the signal sequence S and a portion of the cell wall-binding domain X from protein A, and an amino acid sequence represented by the 31st Ala and the subsequent sequence in SEQ ID NO: 19 (corresponding to "SPA'" of Example 5; see FIGS. 7 and 8 and SEQ ID NOs: 18 and 19), which is obtained by removing the signal sequence S and the whole cell wall-binding domain X from protein A.

Further examples of the "partial sequence" can include amino acid sequences constituting immunoglobulin-binding domains possessed by the protein G and protein L described above.

The immunoglobulin-binding domains of protein A described herein refer to, for example, a region from an amino acid residue at the 37th position to an amino acid residue at the 327th position (domains E to C) in FIG. 1 and a region from an amino acid residue at the 37th position to an amino acid residue at the 355th position (domains E to C) in FIG. 2.

3. DNA Sequence Encoding Protein A-Like Protein

A DNA sequence encoding a protein A-like protein used in the present invention may be any DNA sequence whose translated amino acid sequence constitutes the protein A-like protein. Such a DNA sequence can be obtained by utilizing a method usually used and known in the art, for example, a polymerase chain reaction (hereinafter, abbreviated to PCR) method. Alternatively, it may be synthesized by a chemical synthesis method known in the art (Nucleic acids Res. 1984. 12: 4359) and can further be obtained from DNA libraries. The DNA sequence may have codon substitution by a degenerate codon and does not have to be identical to the original DNA sequence as long as it encodes an identical amino acid when translated in a *Brevibacillus* genus bacterium.

4. Expression Vector

An "expression vector" of the present invention comprises a DNA sequence encoding a protein A-like protein or partial sequence thereof, and a promoter which is operatively linked to the sequence and is capable of functioning in a *Brevibacillus* genus bacterium. The promoter may be any of those capable of functioning in a *Brevibacillus* genus bacterium and is preferably a promoter that is derived from *Escherichia coli, Bacillus subtilis, Brevibacillus* genus, *Staphylococcus* genus, *Streptococcus* genus, *Streptomyces* genus, and *Corynebacterium* genus bacteria and is operative in a *Brevibacillus* genus bacterium, more preferably a promoter of a gene encoding a middle wall protein (MWP), which is a cell wall protein of a *Brevibacillus* genus bacterium, an outer wall protein (OWP), which is also a cell wall protein of a *Brevibacillus* genus bacterium (Non-Patent Document 10), or a *Brevibacillus choshinensis* HPD31 cell wall protein HWP (Ebisu. S et al., J. Bacteriol. 1990. 172: 1312-1320). In Examples, the P5 promoter region "MWP-P5" (see FIGS. 3 and 4 and SEQ ID NOs: 7 and 8) of a *Brevibacillus brevis* cell wall protein MWP shown in Example 1 and the P2 promoter region "MWP-P2" (see FIGS. 7 and 8 and SEQ ID NOs: 18 and 19) of a *Brevibacillus brevis* cell wall protein MWP shown in Example 5 respectively correspond to the "promoter which is capable of functioning a *Brevibacillus* genus bacterium".

Moreover, it is preferred that the "expression vector" should further comprise downstream of the promoter, Shine-Dalgarno and signal sequences which are capable of functioning in a *Brevibacillus* genus bacterium. The expression vector may comprise a marker sequence, if desired.

The "Shine-Dalgarno sequence" following the promoter is preferably a Shine-Dalgarno sequence that is derived from *Escherichia coli, Bacillus subtilis, Brevibacillus* genus, *Staphylococcus* genus, *Streptococcus* genus, *Streptomyces* genus, and *Corynebacterium* genus bacteria and is operative in a *Brevibacillus* genus bacterium, more preferably a Shine-Dalgarno sequence located upstream of a gene encoding a middle wall protein (MWP), which is a cell wall protein of a *Brevibacillus* genus bacterium, an outer wall protein (OWP), which is also a cell wall protein of a *Brevibacillus* genus bacterium, or a *Brevibacillus choshinensis* HPD31 cell wall protein HWP.

The secretion signal peptide-encoding DNA sequence following the Shine-Dalgarno sequence is not particularly limited as long as it is any of DNA sequences encoding secretion signal peptides described below. The DNA sequence does not have to be identical to the original DNA sequence as long as it encodes an identical amino acid when translated in *Brevibacillus brevis*. For example, the secretion signal peptide is preferably a secretion signal peptide that is derived from *Escherichia coli, Bacillus subtilis, Brevibacillus* genus, *Staphylococcus* genus, *Streptococcus* genus, *Streptomyces* genus, and *Corynebacterium* genus bacteria and is operative in a *Brevibacillus* genus bacterium, more preferably a secretion signal peptide of a middle wall protein (MWP), which is a cell wall protein of a *Brevibacillus* genus bacterium, an outer wall protein (OWP), which is also a cell wall protein of a *Brevibacillus* genus bacterium, or a *Brevibacillus choshinensis* HPD31 cell wall protein HWP. Alternatively, the secretion signal peptide may be a conventional secretion signal peptide having a modified amino acid sequence. Specifically, it may be a secretion signal peptide derived from the signal peptide of the middle wall protein (MWP) having the sequence Met-Lys-Lys-Val-Val-Asn-Ser-Val-Leu-Ala-Ser-Ala-Leu-Ala-Leu-Thr-Val-Ala-Pro-Met-Ala-Phe-Ala (SEQ ID NO: 11) modified by the addition or deletion of basic amino acid residues, hydrophobic amino acid residues, and the like, as illustrated by the underlines of the sequence Met-Lys-Lys-<u>Arg-Arg</u>-Val-Val-Asn-Asn-Ser-Val-<u>Leu-Leu</u>-Leu-Leu-Leu-Leu-Ala-Ser-Ala-Leu-Ala-Leu-Thr-Val-Ala-Pro-Met-Ala-Phe-Ala (SEQ ID NO: 12). Alternatively, it may be a secretion signal peptide conventionally used for *Brevibacillus* genus bacterium secreted proteins. Furthermore, the secretion signal peptide may be a signal peptide intrinsically carried by the protein A (FIGS. 1 and 2), that is, Met-Lys-Lys-Lys-Asn-Ile-Tyr-Ser-Ile-Arg-Lys-Leu-Gly-Val-Gly-Ile-Ala-Ser-Val-Thr-Leu-Gly-Thr-Leu-Leu-Ile-Ser-Gly-Gly-Val-Thr-Pro-Ala-Ala-Asn-Ala.

The promoter sequence, the Shine-Dalgarno sequence, and the secretion signal peptide-encoding DNA sequence can be obtained from, for example, a *Brevibacillus* genus bacterium. Preferably, they can be obtained by specific amplification by a PCR method known in the art with the chromosomal DNA of *Brevibacillus brevis* 47 (JCM6285) (see Japanese Patent Laid-Open No. 60-58074), *Brevibacillus brevis* 47K (FERM BP-2308) (see Non-Patent Document 10), *Brevibacillus brevis* 47-5 (FERM BP-1664), *Brevibacillus choshinensis* HPD31 (FERM BP-1087) (see Japanese Patent Laid-Open No. 4-278091), *Brevibacillus choshinensis* HPD31-S (FERM BP-6623), or *Brevibacillus choshinensis* HPD31-OK (FERM BP-4573) (see Japanese Patent Laid-Open No. 6-296485) as a template.

For the "expression vector" of the present invention, it is preferred that any of the promoters, any of the Shine-Dalgarno sequences, any of the signal peptide sequences, and the DNA sequence encoding the protein A-like protein or the partial sequence of the protein A-like protein should be linked operatively within a *Brevibacillus* genus bacterium.

A plasmid vector is preferable as the vector. Specific examples of an available plasmid vector useful for gene expression in a *Brevibacillus* genus bacterium include, but not limited to, pUB110 known in the art as a *Bacillus subtilis* vector or pHY500 (Japanese Patent Laid-Open No. 2-31682), pNY700 (Japanese Patent Laid-Open No. 4-278091), pHY4831 (J. Bacteriol. 1987. 1239-1245), pNU200 (Shigezo Udaka, Nippon Nogeikagaku Kaishi, and Agrochemistry, 1987. 61: 669-676), pNU100 (Appl. Microbiol. Biotechnol., 1989, 30: 75-80), pNU211 (J. Biochem., 1992, 112: 488-491), pNU211R2L5 (Japanese Patent Laid-Open No. 7-170984), pNH301 (Shiga. Y. et al., Appl. Environ. Microbiol. 1992. 58: 525-531), pNH326, pNH400 (Ishihara. T et al., 1995. J. Bacteriol, 177: 745-749), pHT210 (Japanese Patent Laid-Open No. 6-133782), pHT110R2L5 (Appl. Microbiol. Biotechnol., 1994, 42: 358-363), or a shuttle vector pNCO2 of *Escherichia coli* and a *Brevibacillus* genus bacterium (Japanese Patent Laid-Open No. 2002-238569). Alternatively, a method may also be used, which comprises directly incorporating an expression vector containing a promoter and Shine-Dalgarno sequence functioning in a *Brevibacillus* genus bacterium and a DNA sequence encoding a protein of interest, or a gene fragment containing these sequences into the chromosome and causing the expression of the protein of interest (Japanese Patent Laid-Open No. 9-135693). Such a method is a method known in the art, which has already been used for *Bacillus subtilis* and yeast.

In the present invention, a protein A-like protein or protein consisting of a partial sequence thereof may be produced in either a secreted or non-secreted form and preferably, is produced in a form secreted into a culture solution in terms of ease of separation and purification.

For producing the protein A-like protein or protein consisting of a partial sequence thereof in the secreted form, it is preferred that the signal peptide-encoding DNA functioning in a *Brevibacillus* genus bacterium should be added or ligated upstream of DNA encoding the corresponding polypeptide.

5. Transformant

The present invention also provides a *Brevibacillus* genus bacterium transformant, which has been transformed with the expression vector.

An arbitrary *Brevibacillus* genus bacterium is available as a host cell. The *Brevibacillus* genus bacterium includes, but not limited to, *Brevibacillus agri, B. borstelensis, B. brevis, B. centrosporus, B. choshinensis, B. formosus, B. invocatus, B. laterosporus, B. limnophilus, B. parabrevis, B. reuszeri*, and *B. thermoruber*. Preferably, the *Brevibacillus* genus bacterium is selected from the group consisting of a *Brevibacillus brevis* 47 strain (JCM6285), *Brevibacillus brevis* 47K strain (FERM BP-2308), *Brevibacillus brevis* 47-5Q strain (JCM8970), *Brevibacillus choshinensis* HPD31 strain (FERM BP-1087), and *Brevibacillus choshinensis* HPD31-OK strain (FERM BP-4573). Especially, the *Brevibacillus brevis* 47, *Brevibacillus brevis* 47-5Q, or *Brevibacillus choshinensis* HPD31 strain, or a *Brevibacillus choshinensis* HPD31-S strain is suitable.

Mutant strains such as protease-deficient strains or high-expression strains of the *Brevibacillus* genus bacterium may be used according to purposes such as improvement in yields. Specifically, a protease mutant strain *Brevibacillus choshinensis* HPD31-OK derived from *Brevibacillus choshinensis* HPD31 (Japanese Patent Laid-Open No. 6-296485) and *Brevibacillus brevis* 47K obtained as a human salivary amylase-hyperproducing strain (Konishi, H. et al., Appl Microbiol. Biotechnol. 1990. 34: 297-302) can be used. Alternatively, a mutant of any strain included in the *Brevibacillus* genus bacterium group described above may be used.

Of the microorganisms described above, the *Brevibacillus brevis* 47K (FERM BP-2308), *Brevibacillus brevis* 47-5 (FERM BP-1664), *Brevibacillus choshinensis* HPD31 (FERM BP-1087), *Brevibacillus choshinensis* HPD31-S (FERM BP-6623), and *Brevibacillus choshinensis* HPD31-OK (FERM BP-4573) strains have been deposited as their respective accession numbers with International Patent Organism Depositary, National Institute of Advanced Industrial Science and Technology (IPOD; Tsukuba Central 6, 1-1-1 Higashi, Tsukuba, Ibaraki, 305-8566, Japan). The *Brevibacillus brevis* 47 (JCM6285) and *Brevibacillus brevis* 47-5Q (JCM8970) strains can be obtained from Japan Collection of Microorganisms, RIKEN BioResource Center (JCM; 2-1, Hirosawa, Wako, Saitama, 351-0198, Japan).

6. Regulation of Protein Expression

When a heterologous protein is highly expressed in microorganisms including a *Brevibacillus* genus bacterium, an incorrectly folded, inactive protein is often formed. Particularly a protein with many disulfide bonds, when highly expressed therein, is also often insolubilized intra- and extracellularly. On the other hand, it has been known that to express a protein of interest, the insolubilization of the protein of interest and reduction in secretion efficiency thereof can be suppressed by the action of a chaperone protein or disulfide bond isomerase and/or proline isomerase. A method widely attempted is a method comprising allowing protein(s) having disulfide oxidation-reduction activity such as PDI (protein disulfide isomerase) and/or DsbA to act on a protein of interest (Japanese Patent Laid-Open Nos. 63-294796 and 5-336986).

Furthermore, a method is also known, which comprises introducing a gene encoding a protein having disulfide oxidation-reduction activity into a host organism and causing the coexpression of a protein of interest and the protein having disulfide oxidation-reduction activity to thereby produce a protein having correct disulfide bonds (Japanese Patent Laid-Open No. 2000-83670, National Publication of International Patent Application No. 2001-514490, etc).

For the expression of the protein A-like protein or protein consisting of a partial sequence thereof according to the present invention, several kinds of folding-promoting enzymes such as chaperone proteins, disulfide bond oxidoreductases, and/or disulfide isomerases may also be coexpressed during the protein expression in order to reduce burdens on a host cell caused by excessive protein synthesis and smoothly achieve protein secretion. Specifically, *Escherichia coli* DsbA that is involved in protein disulfide bonds and has been thought to be a protein disulfide isomerase analog (Bardwell, J. C. A. et al., Cell. 1991. 67: 582-589; and Kamitani. S et al., EMBO. J. 1992. 11: 57-62) and/or chaperone proteins such as DnaK, DnaJ, and GrpE (Japanese Patent Laid-Open No. 9-180558) can be coexpressed during the protein expression in a *Brevibacillus* genus bacterium. In addition, folding-promoting enzyme(s) such as an enzyme PDI involved in correct polypeptide disulfide bonds (Japanese Patent Application No. 2001-567367), disulfide oxidoreductase (Japanese Patent Laid-Open No. 2003-169675) (Kontinen, V, P. et al., Molecular Microbiology. 1993. 8: 727-737), and/or disulfide isomerase can be expressed simultaneously with the protein to thereby further improve secretion efficiency.

7. Transformant

The *Brevibacillus* genus bacterium used as a host cell in the present invention can be transformed by the method of Takahashi et al (Takahashi. W et al., J. Bacteriol. 1983. 156: 1130-1134), the method of Takagi et al (Takagi. H. et al., 1989. Agric. Biol. Chem., 53: 3099-3100), or the method of Okamoto et al (Okamoto. A. et al., 1997. Biosci. Biotechnol. Biochem. 61: 202-203) known in the art.

A medium used for culturing the obtained transformant is not particularly limited as long as it can produce the protein A-like protein or protein consisting of a partial sequence thereof at high efficiency and high yields. Specifically, carbon and nitrogen sources such as glucose, sucrose, glycerol, polypeptone, meat extracts, yeast extracts, and casamino acid can be employed. In addition, the medium is supplemented, as required, with inorganic salts such as potassium salts, sodium salts, phosphate, magnesium salts, manganese salts, zinc salts, and iron salts. When an auxotrophic host cell is used, nutritional substances necessary for its growth may be added thereto. Moreover, antibiotics such as penicillin, erythromycin, chloramphenicol, and neomycin may also be added, if necessary. Furthermore, a variety of protease inhibitors known in the art, that is, phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetra acetic acid (EDTA), and/or other commercially available protease inhibitors may be added at appropriate concentrations in order to suppress the degradation and low-molecularization of the protein of interest by host-derived protease present within and without the bacterial cell.

A culture temperature is approximately 15 to 42° C., preferably approximately 28 to 37° C. It is desirable that the culture should be performed aerobically under aeration-stirring conditions. However, the transformant may be cultured anaerobically with aeration blocked, if necessary.

8. Acquisition of Protein A-Like Protein

According to the embodiments of the present invention, a large amount of the protein A-like protein or protein consisting of a partial sequence thereof is allowed to accumulate outside of the bacterial cell, that is, in the culture supernatant, by culturing the transformed *Brevibacillus* genus bacterium. Therefore, the protein can be collected and purified in an active form from the culture supernatant. The protein remaining within the bacterial cell and on the bacterial surface can also be extracted by disrupting the bacterium by a method known in the art, for example, a method utilizing ultrasonic waves, French press, or alkaline or SDS treatment. The obtained protein can be purified effectively with use of a protein purification method known in the art, for example, salting-out using ammonium sulfate, sodium sulfate, or the like, concentration with ethanol, acetone, or the like, and a variety of chromatography techniques such as gel filtration, ion exchange, hydroxyapatite, and chromatography techniques utilizing the antibody-binding activity of the protein, and/or the affinity of the protein.

The *Brevibacillus* genus bacterium transformant, which has been transformed with the "expression vector" of the present invention, can stably express the protein and secrete and accumulate the protein in large amounts into the culture supernatant. Specifically, the transformant is cultured in an appropriate medium and can thereby secrete and accumulate into the culture supernatant, a large amount of active protein A that appears around a molecular weight of 40,000 to 50,000 in SDS-PAGE. The process for producing the protein according to the embodiments can achieve a yield of at least approximately 150 mg/L of culture solution, preferably approximately 200 mg/L of culture solution, more preferably approximately 500 mg/L of culture solution, most preferably approximately 1000 or more mg/L of culture solution. The yield, of course, may differ depending on culture conditions, and so on.

9. Immobilization of Protein-Like Protein onto Base Matrix

In the present invention, representative examples of a "base matrix" for immobilizing thereon the protein-like protein or protein consisting of a partial sequence thereof include: but not limited to, inorganic base matrix such as active carbon, glass beads, and silica gel; synthetic polymers or resins such as crosslinked polyvinyl alcohol, crosslinked polyacrylate, crosslinked polyacrylamide, and crosslinked polystyrene; organic base matrix consisting of polysaccharides such as crystalline cellulose, crosslinked cellulose, crosslinked agarose, and crosslinked dextrin; and organic-organic or organic-inorganic composite base matrix that may be obtained with cellulose, polyvinyl alcohol, a saponified ethylene-vinyl acetate copolymer, polyacrylamide, polyacrylic acid, polymethacrylic acid, poly(methyl methacrylate), polyacrylic acid-grafted polyethylene, polyacrylamide-grafted polyethylene, glass, and combinations thereof. Preferably, the base matrix is selected from the group consisting of water and synthetic polymer compounds such as nylon 6, nylon 6,6, nylon 11, polyethylene, poly(vinylidene chloride), poly(vinyl chloride), poly(vinyl acetate), polystyrene, a styrene-divinylbenzene copolymer, styrene-divinylbenzene, poly(trifluoroethylene), poly(chlorotrifluoroethylene), poly(ethylene terephthalate), polypropylene, poly(methyl acrylate), polyacrylic ester, poly(methyl methacrylate), polymethacrylic ester, crosslinked polyacrylate, and crosslinked polyamide. Any of spherical shape, granulated shape, flat membrane shape, fibrous shape, hollow-fibrous shape, and the like can be used effectively as the shape of the base matrix. The spherical or granulated shape is used more preferably in terms of adsorption performance. When the water-insoluble porous material is spherical or granulated in shape, its average particle size is preferably approximately 5 μm to 1000 μm, more preferably approximately 20 to 800 μm, most preferably approximately 30 to 600 μm.

In the present invention, the protein A-like protein or protein consisting of a partial sequence thereof may be immobilized onto the base matrix thorough covalent or noncovalent bond, for example, affinity, association, antigen-antibody reaction, hydrogen bond, or conjugation. Moreover, the immobilization onto the base matrix can be simplified by subjecting the protein to molecular modification such as the addition, substitution, and/or deletion of amino acid residue(s) by means well known by those skilled in the art. The protein A-like protein can be immobilized easily onto the base matrix by introducing, for example, a cysteine residue, into the protein A-like protein molecule.

The immunoglobulin-adsorbing medium obtained by the producing process of the present invention is preferably available as a medium for the purification of immunoglobulin, particularly IgG. Moreover, it may also be applied to disease treatment such as the removal of IgG from blood plasma.

EXAMPLES

Hereinafter, the present invention will be described specifically on the basis of Reference Examples and Examples. However, the scope of the present invention is not intended to be limited to them. To practice the present invention, recombinant DNA preparation and procedures were performed according to the following experiment books, unless otherwise stated: (1) T. Maniatis, E. F. Fritsch, J. Sambrook, "Molecular Cloning/A Laboratory Manual" Vol. 2 (1989), Cold Spring Harbor Laboratory (US); and (2) ed. M. Muramatsu, "Laboratory Manual for Genetic Engineering" Vol. 3 (1996), Maruzen.

Example 1

Cloning of DNA Sequence Encoding Protein A Derived from *Staphylococcus aureus* ATCC 6538P Strain

*Staphylococcus aureus* ATCC 6538P strains were shake-cultured overnight at 37° C. in a T2 liquid medium (1% polypeptone, 0.2% yeast extract, 1% glucose, 0.5% fish extract, pH 7.0). Bacterial cells were collected from the obtained culture solution by centrifugation and then washed twice with 10 mM Tris-HCl buffer solution (pH 8.0). The bacterial cells were suspended in the same buffer solution, then lysed with 1% SDS, and heated at 60° C. for 30 minutes, followed by total genomic DNA extraction by standard methods such as phenol extraction and ethanol precipitation.

Next, two oligonucleotide primers 5'-TTGCTCCCATG-GCTTTCGCTGCGCAACACGATGAAGCT-3' (SEQ ID NO: 5) and 5'-CGGGATCCCTAAAATACAGTTGTAC-CGATGAATGGATT-3' (SEQ ID NO: 6) were prepared on the basis of the DNA sequence information of the protein A gene (Non-Patent Document 6). PCR using these two oligonucleotide primers was performed with the genomic DNA as a template to amplify a DNA fragment (approximately 1.2 kbp (kilobase pair)) encoding a site (hereinafter, referred to as SPA) of protein A except for the signal sequence (S domain) and a portion of the cell wall-binding domain (X domain).

The obtained DNA fragment was digested with restriction enzymes NcoI and BamHI and then separated and collected with an agarose gel.

On the other hand, a *Brevibacillus* expression vector pNH301 (Shiga. Y. et al., Appl. Environ. Microbiol. 1992. 58: 525-531) was also digested with restriction enzymes NcoI and BamHI and then purified and collected, followed by dephosphorylation treatment by alkaline phosphatase treatment.

Figure 4:
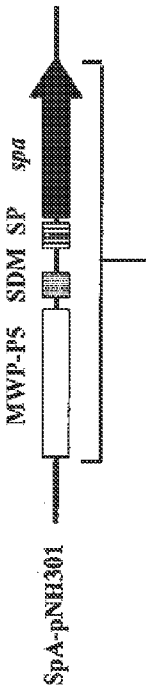
FIG. 4 is a diagram showing the nucleotide sequence and amino acid sequence from a promoter sequence to a protein A (SPA)-encoding region in the protein A (SPA) expression vector (Spa-pNH301)

The SPA-encoding DNA fragment and the expression vector pNH301 treated with the restriction enzymes were ligated with use of T4 DNA ligase to construct a SPA expression plasmid Spa-pNH301 (FIGS. 3 and 4; SEQ ID NOs: 7 and 8). In FIGS. 3 and 4, "MWP-P5" denotes the P5 promoter region of a *Brevibacillus brevis* cell wall protein MWP, "SDM" denotes the SD sequence of the *Brevibacillus brevis* cell wall protein MWP, "SP" denotes the signal peptide sequence of the *Brevibacillus brevis* cell wall protein MWP, "spa" denotes the DNA sequence encoding "SPA", "Nm" denotes the coding region of a neomycin resistance gene, and "Rep/pUB110" denotes the replication origin of the vector pNH301. In FIG. 4, "P5-35" and "P5-10" denote the −35 and −10 regions of the P5 promoter of the *Brevibacillus brevis* cell wall protein MWP, respectively. This Spa-pNH301 was used to transform *Brevibacillus brevis* 47K or *Brevibacillus choshinensis* HPD31-OK strains by a method known in the art.

Example 2

Protein A Expression Test with *Brevibacillus* Genus Bacterium

Figure 5:
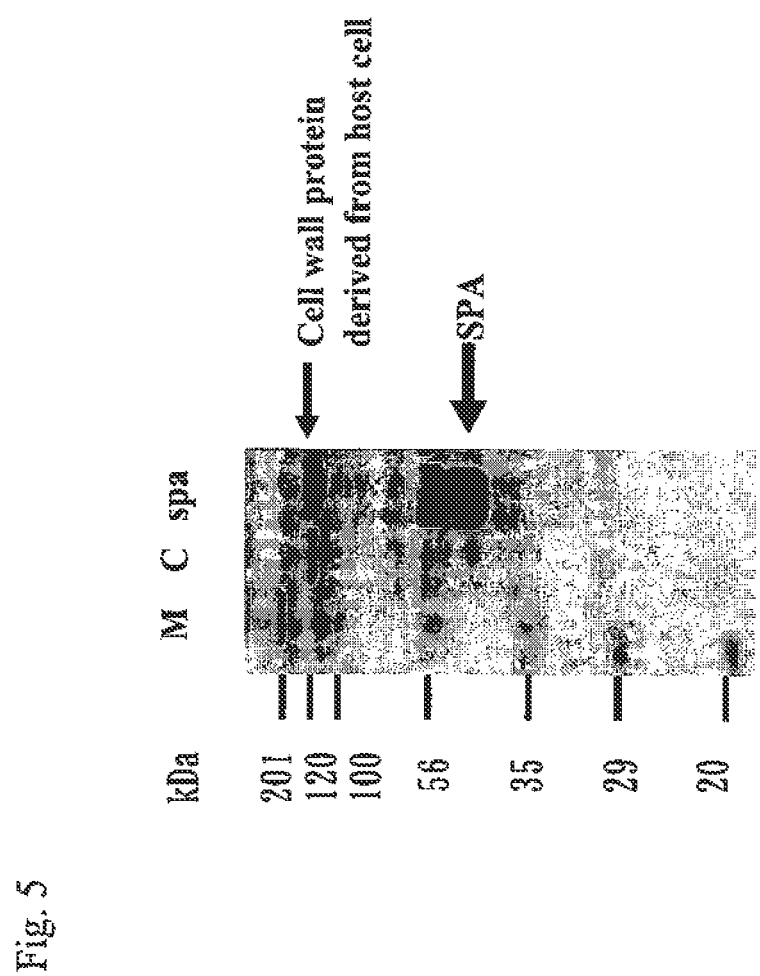
FIG. 5 is a diagram showing a result of SDS-PAGE analysis of protein A (SPA) produced by *Brevibacillus choshinensis* HPD31-OK strains.

The transformant obtained in Example 1 and a *Brevibacillus choshinensis* HPD31-OK strain used as a control, which had only the vector pNH301, were separately cultured at 30° C. for 3 days under aerobic conditions in a 3YC production medium (3% polypeptone S, 0.5% yeast extract, 3% glucose, 0.01% $MgSO_4.7H_2O$, 0.01% $CaCl_2.7H_2O$, 0.001% $MnSO_4.4H_2O$, 0.001% $FeSO_4.7H_2O$, 0.0001% $ZnSO_4.7H_2O$, pH 7.0) supplemented with 60 mg/L neomycin. The culture solutions were centrifuged (10,000 rpm, 4° C., 5 min.) to thereby remove the bacterial cells, and the resulting solutions were then subjected to SDS-PAGE by a standard method under reduction conditions using 10 to 20% gradient gel. After electrophoresis, the gel was stained with CBB to thereby detect a SPA band (FIG. 5). As a result of SDS-PAGE analysis, a large amount of SPA could be confirmed in the culture supernatant thereof.

To express full-length protein A also containing the cell wall-binding domain (X domain) of protein A, the following method can be adopted: the genomic DNA prepared from *Staphylococcus aureus* described in Example 1 is used as a template to amplify a DNA fragment by PCR using two oligonucleotide primers 5'-TTGCTCCCATGGCTTTCGCT-GCGCAACACGATGAAGCT-3' (SEQ ID NO: 5) and 5'-CGCGGATCCTTATAGTTCGCGACGACG-3' (SEQ ID NO: 9) or 5'-CGCGGATCCTCAACGTATATAAGT-TAAAAT-3' (SEQ ID NO: 10). The obtained DNA fragment encoding protein A is ligated between the NcoI and BamHI sites of pNH301 by the method described in Example 1. *Brevibacillus brevis* 47K or *Brevibacillus choshinensis* HPD31-OK strains are transformed with the obtained plasmid to obtain a transformant. This transformant is cultured by the culture method described in Example 2, followed by the confirmation of protein A secreted into the culture solution.

Example 3

Measurement of Antibody-Binding Ability of Protein A Produced by *Brevibacillus* Genus Bacterium To confirm whether SPA produced by the transformant obtained in Example 1 had antibody-binding ability, mouse anti-human IgG antibodies and alkaline phosphatase-labeled rabbit anti-mouse IgG antibodies were used to conduct a binding test.

Figure 6:
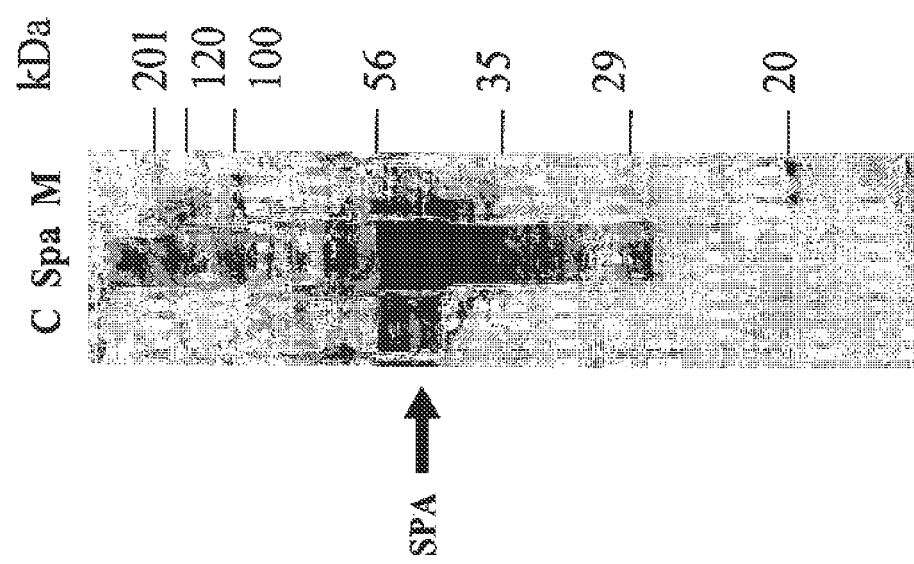
FIG. 6 is a diagram showing a result of an antibody binding test of protein A (SPA) produced by *Brevibacillus choshinensis* HPD31-OK strains.

The *Brevibacillus choshinensis* HPD31-OK strains having either the Spa-pNH301 obtained in Example 1 or the pNH301 used as a control were cultured in the same way as in Example 2, and their respective culture supernatants were subjected to SDS-PAGE and then transferred to a PVDF membrane by a standard method. The membrane was blocked with 3% skimmed milk. An antibody binding test was conducted according to the method of Fahnestock et al (Fahnestock. S. R et al., J. Bacteriol. 1986. 165: 796-804). Detection was performed with an AP color development kit (manufactured by Bio-Rad) according to the instruction manual. As a result, no band was observed for the transformant having only the vector pNH301 used as a comparative control. On the other hand, strong color development was observed at the same mobility as that of SPA, that is, around 42 kDa that had exhibited a dark band on SDS-PAGE by CBB staining, for the transformant having the SPA expression vector Spa-pNH301 (FIG. 6). In FIG. 6, "M" denotes a molecular weight marker, "C" denotes the lane of the *Brevibacillus choshinensis* HPD31-OK strain having the vector pNH301, and Spa denotes the lane of the *Brevibacillus choshinensis* HPD31-OK strain having the SPA expression vector Spa-pNH301. These results demonstrated that a protein with a molecular weight of approximately 42 kDa produced by the *Brevibacillus choshinensis* HPD31-OK strain having the SPA expression vector Spa-pNH301 has antibody-binding activity.

Example 4

Construction of *Brevibacillus* Expression Vector pNK3260

A *Brevibacillus* expression vector pNK3260 was constructed as described below by changing a MWP P5 promoter contained in pNH326 (Ishihara. T et al., 1995. J. Bacteriol, 177: 745-749) to a MWP P2 promoter.

At first, PCR using two oligonucleotide primers 5'-GGAATTCTGATTTCACTTTTTGCATTCTACA-3' (SEQ ID NO: 13) and 5'-AGTGCACTCGCACTTACTGT-3' (SEQ ID NO: 14) was performed with pNH326 as a template to amplify a part of pNH326 except for the MWP P5 promoter. The ends of the amplified fragment were digested with restriction enzymes EcoRI and HindIII. Next, a double-stranded DNA fragment containing a MWP P2 promoter 5'-GGTACCAATTGGCGCCGCAACTTTTGAT-TCGCTCAGGCGTTTAATAGGATGTAATTG TGAGCG-GATAACAATTATTCTGCATGGCTTTCCT-GCGAAAGGAGGTGCACCGCGCTT GCAGGATTCGGGCTTTAAAAAGAAA-GATAGATTAACAACAAATATTCCCCAAGAACA ATTTGTTTATACTGGAGGAGGAGAACA-CAAGGTCATGAAAAAAAGAAGGGTCGTTAA CAGT-GTATTGCTTCTGCTACTGCTAGCTAGTG-CACTCGCACTTACTGTTGCTCCCAT GGCTTTCGCTGCAGGATCCGTC-GACTCTAGACTCGAGGAATTCGGTACCCCGGGTTC GAAATCGATAAGCTTCTGT-3' (SEQ ID NO: 15) was prepared according to a standard method, and the ends thereof were digested with restriction enzymes MunI and HindIII. These two DNA fragments were ligated with use of T4 DNA ligase to construct pNK3260.

Example 5

Cloning of DNA Sequence Encoding Protein A Derived from *Staphylococcus aureus* Cowan I Strain (JCM2179)

Total genomic DNA was extracted from *Staphylococcus aureus* Cowan I strains (JCM2179) in the same way as in Example 1. Next, two oligonucleotide primers 5'-TTGCTC-CCATGGCTTTCGCTGCGCAACACGAT-GAAGCTCAACAA-3' (SEQ ID NO: 16) and 5'-CGG-GATCCCTATTTTGGTGCTTGAGCATCGTTTAGCTTT TTAGCTTCTGCTAAAATT TTC-3' (SEQ ID NO: 17) were prepared on the basis of the DNA sequence information of the protein A gene (Non-Patent Document 2). PCR using these two oligonucleotide primers was performed with the genomic DNA as a template to amplify a DNA fragment (approximately 0.9 kbp) encoding a part (hereinafter, referred to as SPA') of protein A except for the signal sequence (S domain) and the cell wall-binding domain (X domain). The obtained DNA fragment was digested with restriction enzymes NcoI and BamHI and then separated and collected with an agarose gel.

On the other hand, the *Brevibacillus* expression vector pNK3260 constructed in Example 4 was also digested with restriction enzymes NcoI and BamHI and then purified and collected, followed by dephosphorylation treatment by alkaline phosphatase treatment.

Figure 7:
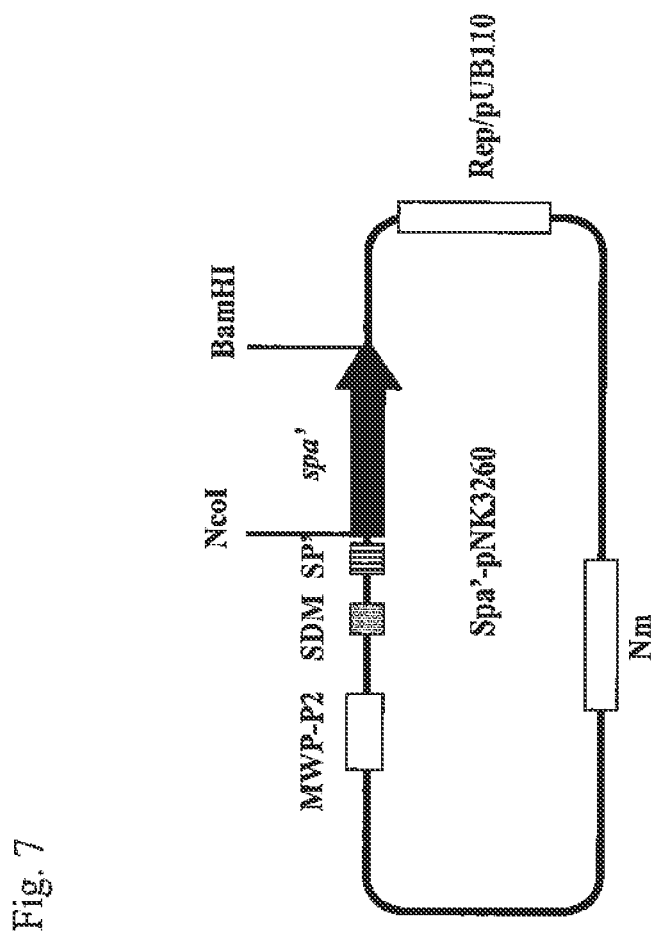
FIG. 7 is a diagram showing a protein A (SPA') expression vector (Spa'-pNK3260)
Figure 8:
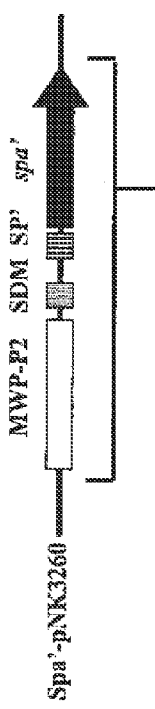
FIG. 8 is a diagram showing a promoter sequence, Shine-Dalgarno sequence, signal peptide-encoding DNA sequence, and protein A (SPA')-encoding DNA sequence in the protein A (SPA') expression vector (Spa'-pNK3260)

The SPA'-encoding DNA fragment and the expression vector pNK3260 after the restriction enzyme treatment were ligated with use of T4 DNA ligase to construct a SPA' expression plasmid Spa'-pNK3260 (FIGS. 7 and 8; SEQ ID NOs: 18 and 19). In FIGS. 7 and 8, "MWP-P2" denotes the P2 promoter region of the *Brevibacillus brevis* cell wall protein MWP, "SDM" denotes the SD sequence of the *Brevibacillus brevis* cell wall protein MWP, "SP'" denotes a modified signal peptide sequence partially modified from the signal peptide sequence of the *Brevibacillus brevis* cell wall protein MWP, "spa'" denotes the DNA sequence encoding SPA', "Nm" denotes the coding region of a neomycin resistance gene, and "Rep/pUB110" denotes the replication origin of the vector pNK3260. In FIG. 8, "P2-35" and "P2-10" denote the −35 and −10 regions of the P2 promoter of the *Brevibacillus brevis* cell wall protein MWP, respectively.

This Spa'-pNK3260 was used to transform *Brevibacillus choshinensis* HPD31-OK strains by a method known in the art.

Example 6

Figure 9:
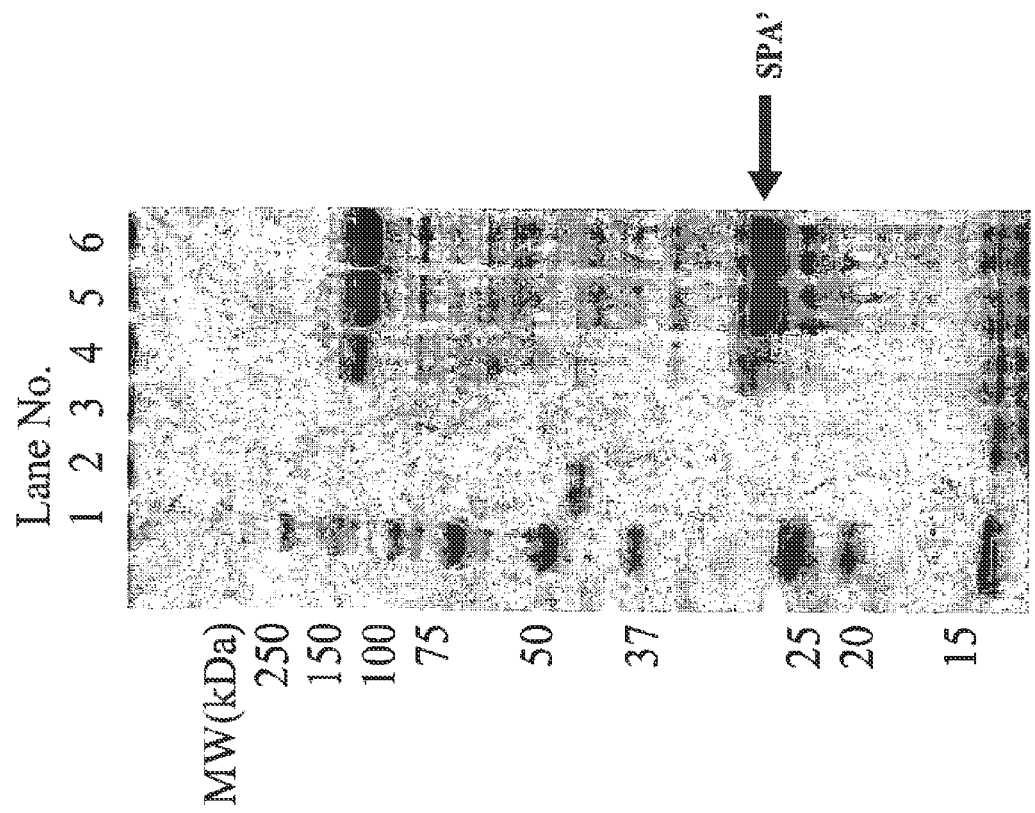
FIG. 9 is a diagram showing a result of SDS-PAGE analysis of the behavior and accumulating amount of protein A (SPA') in a culture solution produced by *Brevibacillus choshinensis* HPD31-OK strains.

Behavior of Protein A in Culture Solution Expressed and Secreted by *Brevibacillus* Genus Bacterium The transformant obtained in Example 5 was cultured at 30° C. under aerobic conditions in a 3YC production medium (3% polypeptone S, 0.5% yeast extract, 3% glucose, 0.01% $MgSO_4.7H_2O$, 0.01% $CaCl_2.7H_2O$, 0.001% $MnSO_4.4H_2O$, 0.001% $FeSO_4.7H_2O$, 0.0001% $ZnSO_4.7H_2O$, pH 7.0) supplemented with 60 mg/L neomycin. The culture solution was sampled after 24, 48, 72, and 78 hours from the initiation of the culture and centrifuged (10,000 rpm, 4° C., 5 min.) to thereby remove the bacterial cells, and the resulting solutions were then subjected to SDS-PAGE by a standard method under reduction conditions using 10 to 20% gradient gel. After electrophoresis, the gel was stained with CBB to thereby detect a SPA' band (FIG. 9). In FIG. 9, "Lane No. 1" denotes a molecular weight marker, "Lane No. 2" denotes a lane showing the migration of 0.52 μg of protein A (rPA-50; manufactured by Repligen) used as a control, "Lane No. 3" denotes a lane showing the migration of 1 μl of the culture supernatant of the *Brevibacillus choshinensis* HPD31-OK strain having the SPA' expression vector Spa'-pNK3260 after a lapse of 24 hours from the initiation of the culture, "Lane No. 4" denotes a lane showing the migration of 1 μl of the culture supernatant thereof after a lapse of 48 hours from the initiation of the culture, "Lane No. 5" denotes a lane showing the migration of 1 μl of the culture supernatant thereof after a lapse of 72 hours from the initiation of the culture, and "Lane No. 6" denotes a lane showing the migration of 1 μl of the culture supernatant thereof after a lapse of 78 hours from the initiation of the culture.

As a result of SDS-PAGE analysis, SPA' of interest was expressed in large amounts on 48 hours after the initiation of the culture (Lane No. 4) and showed increase in concentration from then on. Finally, it accumulated at a concentration of approximately 2 g/L in the culture supernatant. The concentration of SPA' in the culture supernatant was measured with a ChemiDoc XRS system (Bio-Rad) by using the band of 0.52 μg of protein A (rPA-50; manufactured by Repligen) migrating in Lane No. 2 as a control.

Example 7

Confirmation of N-Terminal Amino Acid Sequence of Protein A Produced by Transformant The SPA' band seen around a molecular weight of 33 kDa in Lane No. 6 in the SDS-PAGE gel shown in FIG. 9 was analyzed for its N-terminal 10-residue amino acid sequence according to a standard method. As a result, this sequence was consistent with the 37th Ala and the subsequent sequence in the amino acid sequence of protein A represented by SEQ ID NO: 2, demonstrating that the secretion signal sequence was accurately removed.

Example 8

Antibody-Binding Activity of Protein A Produced by Transformant

One-L of the supernatant of a culture solution obtained from 78-hour culture performed in the same way as in Example 6 was subjected to cation-exchange chromatography (CM-Sepharose; Amersham Biosciences) and separated by 0 to 1 M sodium chloride concentration gradient at pH 7.0. Next, a SPA' fraction was collected, then subjected to hydrophobic chromatography (Phenyl-Sepharose; Amersham Biosciences), and separated by 1 to 0 M ammonium sulfate concentration gradient at pH 7.0. The SPA' fraction was further collected and subjected to gel filtration chromatography (HiLoad 16/60 Superdex 75 pg; Amersham Biosciences), followed by the collection of the SPA' fraction. Approximately 100 mg of SPA', which exhibited a single band in SDS-PAGE, was prepared by these purification procedures.

The SPA' thus prepared was evaluated for its human IgG-binding activity as described below. At first, the SPA' was diluted to 5 μg/mL with a PBS buffer solution (Takara Bio Inc), and 100-μL aliquots thereof were dispensed to a 96-well immunoplate (NUNC). After reaction at 37° C. for 1 hour, the plate was washed twice with a PBS buffer solution (250 μL) and blocked overnight at 4° C. by the addition of 250 μL of 3% bovine serum albumin/PBS solution. Subsequently, 100 μl of 25 μg/mL human IgG (Sigma) solution prepared with a PBS buffer solution containing 0.1% BSA was added thereto. After reaction at 37° C. for 1.5 hours, the plate was washed with a PBS buffer solution containing 0.01% Tween 20. To this plate, 100 μl of a solution of HRP-labeled protein L (0.3 mg/ml; Sigma) diluted 2000-fold with a PBS buffer solution was added. After reaction at 37° C. for 1.5 hours, the plate was washed with a PBS buffer solution containing 0.01% Tween 20. The plate was further supplemented with 100 μl of a chromogenic substrate[2,2'-azinodi(3-ethylbenzothiazoline-6-sulfonic acid) ammonium salt] solution (SIGMA) and reacted for 20 minutes in the dark, followed by the measurement of absorbance at 405 nm. At this time, the same procedures were conducted on protein A (rPA-50; manufactured by Repligen) as a control to compare their measurement values. As a result, the human IgG-binding activity of the thus-prepared SPA' per unit mass was approximately 97% of that of the protein A manufactured by Repligen, demonstrating that they have almost equivalent activity.

These results show that the process for producing protein A according to Examples can achieve productivity exceeding the previously reported expression levels of recombinant protein A in *Escherichia coli* and *Bacillus subtilis* and can solve the problem of low productivity conventionally presented.

The invention claimed is:

1. An isolated DNA sequence comprising
   a promoter which has a promoter activity when said isolated DNA sequence is transformed into a *Brevibacillus* genus bacterium, and
   a DNA sequence encoding a protein A-like protein, wherein said protein A-like protein lacks the cell wall-binding domain X from protein A, and wherein the protein A-like protein is selected from the group consisting of proteins (a) to (c):
   (a) a protein with immunoglobulin-binding activity, which comprises an amino acid sequence having at least 95% amino acid sequence identity to the amino acid sequence of either SEQ ID NO: 2 or SEQ ID NO: 4 without cell wall-binding domain X,
   (b) a protein with immunoglobulin-binding activity, which comprises an arbitrary portion of the amino acid sequence that constitutes the protein (a), and
   (c) a partial sequence of protein A.

2. An isolated DNA sequence, comprising the isolated DNA sequence of claim 1 but in which the protein A-like protein encoded by the DNA sequence also lacks.

3. The DNA sequence according to claim 1,
   wherein the promoter is a promoter of a cell wall protein of a *Brevibacillus* genus bacterium, and
   the DNA sequence further comprises downstream of the promoter, a Shine-Dalgarno sequence which is capable of functioning in a *Brevibacillus* genus bacterium and a secretion signal peptide-encoding DNA sequence which is capable of functioning in a *Brevibacillus* genus bacterium.

4. An expression vector comprising a DNA sequence according to claim 1.

5. A *Brevibacillus* genus bacterium transformant comprising an expression vector according to claim 4.

6. The transformant according to claim 5,
   wherein the *Brevibacillus* genus bacterium is selected from the group consisting of a *Brevibacillus brevis* 47 train (JCM6285), *Brevibacillus brevis* 47K strain (FERM BP-2308), *Brevibacillus brevis* 47-5Q strain (JCM8970), *Brevibacillus choshinensis* HPD31 strain (FERM BP-1087), and *Brevibacillus choshinensis* HPD31-OK strain (FERM BP-4573), and mutants derived from these strains.

7. A process for producing a protein A-like protein, comprising culturing a transformant according to claim 5 and collecting a protein A-like protein produced and secreted by the transformant.

8. A process for producing an immunoglobulin-adsorbing medium, comprising producing a protein A-like protein by a producing process according to claim 7 and immobilizing the protein A-like protein onto an appropriate base matrix.

* * * * *

SEQUENCE LISTING

<160> NUMBER OF SEQ ID NOS: 19

<210> SEQ ID NO 1
<211> LENGTH: 1527
<212> TYPE: DNA
<213> ORGANISM: Staphylococcus aureus

<400> SEQUENCE: 1

```
ttgaaaaaga aaacattta ttcaattcgt aaactaggtg taggtattgc atctgtaact      60
ttaggtacat tacttatatc tggtggcgta acacctgctg caaatgctgc gcaacacgat    120
gaagctcaac aaaatgcttt ttatcaagtg ttaaatatgc ctaacttaaa cgctgatcaa    180
cgtaatggtt ttatccaaag ccttaaagat gatccaagcc aaagtgctaa cgttttaggt    240
gaagctcaaa aacttaatga ctctcaagct ccaaaagctg atgcgcaaca aaataagttc    300
aacaaagatc aacaaagcgc cttctatgaa atcttgaaca tgcctaactt aaacgaagag    360
caacgcaatg gtttcattca aagtcttaaa gacgatccaa gccaaagcac taacgtttta    420
ggtgaagcta aaaaattaaa cgaatctcaa gcaccgaaag ctgacaacaa tttcaacaaa    480
gaacaacaaa atgctttcta tgaaatcttg aacatgccta acttgaacga agaacaacgc    540
aatggtttca tccaaagctt aaaagatgac ccaagtcaaa gtgctaacct tttagcagaa    600
gctaaaaagt taaatgaatc tcaagcaccg aaagctgata caaattcaa caaagaacaa    660 caaaatgctt tctatgaaat cttacattta cctaacttaa atgaagaaca acgcaatggt    720
ttcatccaaa gcttaaaaga tgacccaagc caaagcgcta accttttagc agaagctaaa    780
aagctaaatg atgcacaagc accaaaagct gacaacaaat tcaacaaaga acaacaaaat    840
gctttctatg aaatttttaca tttacctaac ttaactgaag aacaacgtaa cggcttcatc    900
caaagcctta agacgatcc ttcagtgagc aaagaaattt tagcagaagc taaaaagcta    960
aacgatgctc aagcaccaaa agaggaagac aacaacaagc ctggtaaaga agacggcaac   1020
aaacctggta agaagacgg caacaaacct ggtaaagaag acaacaaaaa acctggcaaa   1080
gaagacggca acaaacctgg taagaagac aacaaaaaac ctggcaaaga agatggcaac   1140
aaacctggta agaagacgg caacaagcct ggtaaagaag atggcaacaa gcctggtaaa   1200
gaagatggca acaagcctgg taaagaagac ggcaacggag tacatgtcgt taaacctggt   1260
gatacagtaa atgacattgc aaaagcaaac ggcactactg ctgacaaaat tgctgcagat   1320
aacaaattag ctgataaaaa catgatcaaa cctggtcaag aacttgttgt tgataagaag   1380
caaccagcaa accatgcaga tgctaacaaa gctcaagcat taccagaaac tggtgaagaa   1440
aatccattca tcggtacaac tgtatttggt ggattatcat tagcgttagg tgcagcgtta   1500
ttagctggac gtcgtcgcga actataa                                       1527
```

<210> SEQ ID NO 2
<211> LENGTH: 508

<212> TYPE: PRT
<213> ORGANISM: Staphylococcus aureus

<400> SEQUENCE: 2

```
Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Lys Phe Asn Lys Asp Gln Gln Ser Ala Phe Tyr Glu Ile Leu
            100                 105                 110

Asn Met Pro Asn Leu Asn Glu Glu Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ala Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Gly Asn Lys Pro Gly Lys Glu Asp Gly Asn Lys Pro Gly Lys
            340                 345                 350

Glu Asp Asn Lys Lys Pro Gly Lys Glu Asp Gly Asn Lys Pro Gly Lys
        355                 360                 365

Glu Asp Asn Lys Lys Pro Gly Lys Glu Asp Gly Asn Lys Pro Gly Lys
    370                 375                 380

Glu Asp Gly Asn Lys Pro Gly Lys Glu Asp Gly Asn Lys Pro Gly Lys
385                 390                 395                 400
```

```
Glu Asp Gly Asn Lys Pro Gly Lys Glu Asp Gly Asn Gly Val His Val
                405                 410                 415
Val Lys Pro Gly Asp Thr Val Asn Asp Ile Ala Lys Ala Asn Gly Thr
            420                 425                 430
Thr Ala Asp Lys Ile Ala Ala Asp Asn Lys Leu Ala Asp Lys Asn Met
        435                 440                 445
Ile Lys Pro Gly Gln Glu Leu Val Val Asp Lys Lys Gln Pro Ala Asn
    450                 455                 460
His Ala Asp Ala Asn Lys Ala Gln Ala Leu Pro Glu Thr Gly Glu Glu
465                 470                 475                 480
Asn Pro Phe Ile Gly Thr Thr Val Phe Gly Leu Ser Leu Ala Leu
                485                 490                 495
Gly Ala Ala Leu Leu Ala Gly Arg Arg Arg Glu Leu
            500                 505

<210> SEQ ID NO 3
<211> LENGTH: 1419
<212> TYPE: DNA
<213> ORGANISM: Staphylococcus aureus

<400> SEQUENCE: 3
ttgaaaaaga aaaaaattta ttcaattcgt aaactaggtg taggtattgc atctgtaact      60
ttaggtacat tacttatatc tggtggcgta acacctgctg caaatgctgc gcaacacgat    120
gaagctcaac aaaatgcttt ttatcaagtg ttaaatatgc ctaacttaaa cgctgatcaa    180
cgtaatggtt ttatccaaag ccttaaagat gatccaagcc aaagtgctaa cgttttaggt    240
gaagctcaaa aacttaatga ctctcaagct ccaaaagctg atgcgcaaca aaataagttc    300
aacaaagatc aacaaagcgc cttctatgaa atcttgaaca tgcctaactt aaacgaagag    360
caacgcaatg gtttcattca agtcttaaaa gacgatccaa gccaaagcac taacgtttta    420
ggtgaagcta aaaattaaa cgaatctcaa gcaccgaaag ctgacaacaa tttcaacaaa    480
gaacaacaaa atgctttcta tgaaatcttg aacatgccta acttgaacga gaacaacgc    540
aatggtttca tccaaagctt aaaagatgac ccaagccaaa gcgctaacct tttagcagaa    600
gctaaaaagc taaatgatgc acaagcacca aaagctgaca caaattcaa caagaacaa    660
caaaatgctt tctatgaaat tttacattta cctaacttaa ctgaagaaca acgtaacggc    720
ttcatccaaa gccttaaaga cgatccttca gtgagcaaag aaattttagc agaagctaaa    780
aagctaaacg atgctcaagc accaaaagag gaagacaaca caagcctgg taaagaagac    840
ggcaacaaac ctggtaaaga gacggcaac aaacctggta agaagacaa caaaaaaccct    900
ggcaaagaag acggcaacaa acctggtaaa gaagacaaca aaaaacctgg caaagaagat    960
ggcaacaaac ctggtaaaga gacggcaac aagcctggta agaagatgg caacaagcct   1020
ggtaaagaag atggcaacaa gcctggtaaa gaagacggca acggagtaca tgtcgttaaa   1080
cctggtgata cagtaaatga cattgcaaaa gcaaacggca ctactgctga caaaattgct   1140
gcagataaca aattagctga taaaaacatg atcaaacctg gtcaagaact tgttgttgat   1200
aagaagcaac cagcaaacca tgcagatgct aacaaagctc aagcattacc agaaactggt   1260
gaagaaaatc cattcatcgg tacaactgta tttggtggat tatcattagc gttaggtgca   1320
gcgttattag ctggacgtcc gtcgccgaac tataaaaaca acaatacac aacgatagat   1380
atcattttat ccaaaccaat tttaacttat atacgttga                          1419
```

```
<210> SEQ ID NO 4
<211> LENGTH: 472
<212> TYPE: PRT
<213> ORGANISM: Staphylococcus aureus

<400> SEQUENCE: 4

Met Lys Lys Lys Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
            35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Lys Phe Asn Lys Asp Gln Gln Ser Ala Phe Tyr Glu Ile Leu
            100                 105                 110

Asn Met Pro Asn Leu Asn Glu Glu Gln Arg Asn Gly Phe Ile Gln Ser
            115                 120                 125

Leu Lys Asp Asp Pro Ser Gln Ser Thr Asn Val Leu Gly Glu Ala Lys
130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ala Glu Ala Lys Lys Leu Asn Asp Ala Gln
            195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Thr Glu Glu Gln Arg Asn Gly
225                 230                 235                 240

Phe Ile Gln Ser Leu Lys Asp Asp Pro Ser Val Ser Lys Glu Ile Leu
                245                 250                 255

Ala Glu Ala Lys Lys Leu Asn Asp Ala Gln Ala Pro Lys Glu Glu Asp
            260                 265                 270

Asn Asn Lys Pro Gly Lys Glu Asp Asn Lys Pro Gly Lys Glu Asp
            275                 280                 285

Gly Asn Lys Pro Gly Lys Glu Asp Asn Lys Pro Gly Lys Glu Asp
    290                 295                 300

Gly Asn Lys Pro Gly Lys Glu Asp Asn Lys Pro Gly Lys Glu Asp
305                 310                 315                 320

Gly Asn Lys Pro Gly Lys Glu Asp Asn Lys Pro Gly Lys Glu Asp
                325                 330                 335

Gly Asn Lys Pro Gly Lys Glu Asp Gly Asn Lys Pro Gly Lys Glu Asp
            340                 345                 350

Gly Asn Gly Val His Val Val Lys Pro Gly Asp Thr Val Asn Asp Ile
            355                 360                 365

Ala Lys Ala Asn Gly Thr Thr Ala Asp Lys Ile Ala Ala Asp Asn Lys
    370                 375                 380
```

-continued

```
Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
            405                 410                 415

Pro Glu Thr Gly Glu Glu Asn Pro Phe Ile Gly Thr Thr Val Phe Gly
        420                 425                 430

Gly Leu Ser Leu Ala Leu Gly Ala Ala Leu Leu Ala Gly Arg Pro Ser
        435                 440                 445

Pro Asn Tyr Lys Asn Lys Gln Tyr Thr Thr Ile Asp Ile Ile Leu Ser
    450                 455                 460

Lys Pro Ile Leu Thr Tyr Ile Arg
465                 470

<210> SEQ ID NO 5
<211> LENGTH: 38
<212> TYPE: DNA
<213> ORGANISM: Artificial Sequence
<220> FEATURE:
<223> OTHER INFORMATION: chemically-synthesized PCR primer

<400> SEQUENCE: 5
ttgctcccat ggctttcgct gcgcaacacg atgaagct                      38

<210> SEQ ID NO 6
<211> LENGTH: 38
<212> TYPE: DNA
<213> ORGANISM: Artificial Sequence
<220> FEATURE:
<223> OTHER INFORMATION: chemically-synthesized PCR primer

<400> SEQUENCE: 6
cgggatccct aaaatacagt tgtaccgatg aatggatt                      38

<210> SEQ ID NO 7
<211> LENGTH: 1418
<212> TYPE: DNA
<213> ORGANISM: Brevibacillus brevis
<220> FEATURE:
<221> NAME/KEY: CDS
<222> LOCATION: (162)..(1418)
<220> FEATURE:
<221> NAME/KEY: -10_signal
<222> LOCATION: (31)..(34)
<220> FEATURE:
<221> NAME/KEY: -35_signal
<222> LOCATION: (19)..(23)
<220> FEATURE:
<221> NAME/KEY: RBS
<222> LOCATION: (141)..(151)
<220> FEATURE:
<221> NAME/KEY: RBS
<222> LOCATION: (50)..(60)

<400> SEQUENCE: 7
caggggaata tactagagat ttttaacaca aaaagcgagg ctttcctgcg aaaggaggtg    60
acacgcgctt gcaggattcg ggctttaaaa agaaagatag attaacaaca atattccccc   120
aagaacaatt tgtttatact agaggaggag aacacaaggt t atg aaa aag gtc gtt   176
                                             Met Lys Lys Val Val
                                               1               5 aac agt gta ttg gct agt gca ctc gca ctt act gtt gct cca atg gct    224
Asn Ser Val Leu Ala Ser Ala Leu Ala Leu Thr Val Ala Pro Met Ala
             10                  15                  20 ttc gct gcg caa cac gat gaa gct caa caa aat gct ttt tat caa gtg    272
Phe Ala Ala Gln His Asp Glu Ala Gln Gln Asn Ala Phe Tyr Gln Val
```

```
                    25                  30                  35
tta aat atg cct aac tta aac gct gat caa cgt aat ggt ttt atc caa        320
Leu Asn Met Pro Asn Leu Asn Ala Asp Gln Arg Asn Gly Phe Ile Gln
            40                  45                  50 agc ctt aaa gat gat cca agc caa agt gct aac gtt tta ggt gaa gct        368
Ser Leu Lys Asp Asp Pro Ser Gln Ser Ala Asn Val Leu Gly Glu Ala
        55                  60                  65 caa aaa ctt aat gac tct caa gct cca aaa gct gat gcg caa caa aat        416
Gln Lys Leu Asn Asp Ser Gln Ala Pro Lys Ala Asp Ala Gln Gln Asn
70                  75                  80                  85 aag ttc aac aaa gat caa caa agc gcc ttc tat gaa atc ttg aac atg        464
Lys Phe Asn Lys Asp Gln Gln Ser Ala Phe Tyr Glu Ile Leu Asn Met
                90                  95                 100 cct aac tta aac gaa gag caa cgc aat ggt ttc att caa agt ctt aaa        512
Pro Asn Leu Asn Glu Glu Gln Arg Asn Gly Phe Ile Gln Ser Leu Lys
            105                 110                 115 gac gat cca agc caa agc act aac gtt tta ggt gaa gct aaa aaa tta        560
Asp Asp Pro Ser Gln Ser Thr Asn Val Leu Gly Glu Ala Lys Lys Leu
        120                 125                 130 aac gaa tct caa gca ccg aaa gct gac aac aat ttc aac aaa gaa caa        608
Asn Glu Ser Gln Ala Pro Lys Ala Asp Asn Asn Phe Asn Lys Glu Gln
135                 140                 145 caa aat gct ttc tat gaa atc ttg aac atg cct aac ttg aac gaa gaa        656
Gln Asn Ala Phe Tyr Glu Ile Leu Asn Met Pro Asn Leu Asn Glu Glu
150                 155                 160                 165 caa cgc aat ggt ttc atc caa agc tta aaa gat gac cca agc caa agc        704
Gln Arg Asn Gly Phe Ile Gln Ser Leu Lys Asp Asp Pro Ser Gln Ser
                170                 175                 180 gct aac ctt tta gca gaa gct aaa aag cta aat gat gca caa gca cca        752
Ala Asn Leu Leu Ala Glu Ala Lys Lys Leu Asn Asp Ala Gln Ala Pro
            185                 190                 195 aaa gct gac aac aaa ttc aac aaa gaa caa caa aat gct ttc tat gaa        800
Lys Ala Asp Asn Lys Phe Asn Lys Glu Gln Gln Asn Ala Phe Tyr Glu
        200                 205                 210 att tta cat tta cct aac tta act gaa gaa caa cgt aac ggc ttc atc        848
Ile Leu His Leu Pro Asn Leu Thr Glu Glu Gln Arg Asn Gly Phe Ile
215                 220                 225 caa agc ctt aaa gac gat cct tca gtg agc aaa gaa att tta gca gaa        896
Gln Ser Leu Lys Asp Asp Pro Ser Val Ser Lys Glu Ile Leu Ala Glu
230                 235                 240                 245 gct aaa aag cta aac gat gct caa gca cca aaa gag gaa gac aac aac        944
Ala Lys Lys Leu Asn Asp Ala Gln Ala Pro Lys Glu Glu Asp Asn Asn
                250                 255                 260 aag cct ggt aaa gaa gac ggc aac aaa cct ggt aaa gaa gac ggc aac        992
Lys Pro Gly Lys Glu Asp Gly Asn Lys Pro Gly Lys Glu Asp Gly Asn
            265                 270                 275 aaa cct ggt aaa gaa gac aac aaa aaa cct ggc aaa gaa gac ggc aac       1040
Lys Pro Gly Lys Glu Asp Asn Lys Lys Pro Gly Lys Glu Asp Gly Asn
        280                 285                 290 aaa cct ggt aaa gaa gac aac aaa aaa cct ggc aaa gaa gat ggc aac       1088
Lys Pro Gly Lys Glu Asp Asn Lys Lys Pro Gly Lys Glu Asp Gly Asn
295                 300                 305 aaa cct ggt aaa gaa gac ggc aac aag cct ggt aaa gaa gat ggc aac       1136
Lys Pro Gly Lys Glu Asp Gly Asn Lys Pro Gly Lys Glu Asp Gly Asn
310                 315                 320                 325 aag cct ggt aaa gaa gat ggc aac aag cct ggt aaa gaa gac ggc aac       1184
Lys Pro Gly Lys Glu Asp Gly Asn Lys Pro Gly Lys Glu Asp Gly Asn
                330                 335                 340 gga gta cat gtc gtt aaa cct ggt gat aca gta aat gac att gca aaa       1232
```

```
Gly Val His Val Val Lys Pro Gly Asp Thr Val Asn Asp Ile Ala Lys
            345                 350                 355 gca aac ggc act act gct gac aaa att gct gca gat aac aaa tta gct      1280
Ala Asn Gly Thr Thr Ala Asp Lys Ile Ala Ala Asp Asn Lys Leu Ala
            360                 365                 370 gat aaa aac atg atc aaa cct ggt caa gaa ctt gtt gtt gat aag aag      1328
Asp Lys Asn Met Ile Lys Pro Gly Gln Glu Leu Val Val Asp Lys Lys
375                 380                 385 caa cca gca aac cat gca gat gct aac aaa gct caa gca tta cca gaa      1376
Gln Pro Ala Asn His Ala Asp Ala Asn Lys Ala Gln Ala Leu Pro Glu
390                 395                 400                 405 act ggt gaa gaa aat cca ttc atc ggt aca act gta ttt tag              1418
Thr Gly Glu Glu Asn Pro Phe Ile Gly Thr Thr Val Phe
                410                 415

<210> SEQ ID NO 8
<211> LENGTH: 418
<212> TYPE: PRT
<213> ORGANISM: Brevibacillus brevis

<400> SEQUENCE: 8

Met Lys Lys Val Val Asn Ser Val Leu Ala Ser Ala Leu Ala Leu Thr
1               5                   10                  15

Val Ala Pro Met Ala Phe Ala Ala Gln His Asp Glu Ala Gln Gln Asn
            20                  25                  30

Ala Phe Tyr Gln Val Leu Asn Met Pro Asn Leu Asn Ala Asp Gln Arg
        35                  40                  45

Asn Gly Phe Ile Gln Ser Leu Lys Asp Asp Pro Ser Gln Ser Ala Asn
    50                  55                  60

Val Leu Gly Glu Ala Gln Lys Leu Asn Asp Ser Gln Ala Pro Lys Ala
65                  70                  75                  80

Asp Ala Gln Gln Asn Lys Phe Asn Lys Asp Gln Ser Ala Phe Tyr
                85                  90                  95

Glu Ile Leu Asn Met Pro Asn Leu Asn Glu Glu Gln Arg Asn Gly Phe
            100                 105                 110

Ile Gln Ser Leu Lys Asp Asp Pro Ser Gln Ser Thr Asn Val Leu Gly
        115                 120                 125

Glu Ala Lys Lys Leu Asn Glu Ser Gln Ala Pro Lys Ala Asp Asn Asn
    130                 135                 140

Phe Asn Lys Glu Gln Gln Asn Ala Phe Tyr Glu Ile Leu Asn Met Pro
145                 150                 155                 160

Asn Leu Asn Glu Glu Gln Arg Asn Gly Phe Ile Gln Ser Leu Lys Asp
                165                 170                 175

Asp Pro Ser Gln Ser Ala Asn Leu Leu Ala Glu Ala Lys Lys Leu Asn
            180                 185                 190

Asp Ala Gln Ala Pro Lys Ala Asp Asn Lys Phe Asn Lys Glu Gln Gln
        195                 200                 205

Asn Ala Phe Tyr Glu Ile Leu His Leu Pro Asn Leu Thr Glu Glu Gln
    210                 215                 220

Arg Asn Gly Phe Ile Gln Ser Leu Lys Asp Asp Pro Ser Val Ser Lys
225                 230                 235                 240

Glu Ile Leu Ala Glu Ala Lys Lys Leu Asn Asp Ala Gln Ala Pro Lys
                245                 250                 255

Glu Glu Asp Asn Asn Lys Pro Gly Lys Glu Asp Gly Asn Lys Pro Gly
            260                 265                 270

Lys Glu Asp Gly Asn Lys Pro Gly Lys Glu Asp Asn Lys Lys Pro Gly
```

```
                275                 280                 285
Lys Glu Asp Gly Asn Lys Pro Gly Lys Glu Asp Asn Lys Pro Gly
    290                 295                 300
Lys Glu Asp Gly Asn Lys Pro Gly Lys Glu Asp Gly Asn Lys Pro Gly
305                 310                 315                 320
Lys Glu Asp Gly Asn Lys Pro Gly Lys Glu Asp Gly Asn Lys Pro Gly
                325                 330                 335
Lys Glu Asp Gly Asn Gly Val His Val Val Lys Pro Gly Asp Thr Val
            340                 345                 350
Asn Asp Ile Ala Lys Ala Asn Gly Thr Thr Ala Asp Lys Ile Ala Ala
        355                 360                 365
Asp Asn Lys Leu Ala Asp Lys Asn Met Ile Lys Pro Gly Gln Glu Leu
    370                 375                 380
Val Val Asp Lys Lys Gln Pro Ala Asn His Ala Asp Ala Asn Lys Ala
385                 390                 395                 400
Gln Ala Leu Pro Glu Thr Gly Glu Glu Asn Pro Phe Ile Gly Thr Thr
                405                 410                 415
Val Phe

<210> SEQ ID NO 9
<211> LENGTH: 27
<212> TYPE: DNA
<213> ORGANISM: Artificial Sequence
<220> FEATURE:
<223> OTHER INFORMATION: chemically-synthesized PCR primer

<400> SEQUENCE: 9
cgcggatcct tatagttcgc gacgacg                                       27

<210> SEQ ID NO 10
<211> LENGTH: 30
<212> TYPE: DNA
<213> ORGANISM: Artificial Sequence
<220> FEATURE:
<223> OTHER INFORMATION: chemically-synthesized PCR primer

<400> SEQUENCE: 10
cgcggatcct caacgtatat aagttaaaat                                    30

<210> SEQ ID NO 11
<211> LENGTH: 23
<212> TYPE: PRT
<213> ORGANISM: Brevibacillus brevis

<400> SEQUENCE: 11

Met Lys Lys Val Val Asn Ser Val Leu Ala Ser Ala Leu Ala Leu Thr
1               5                   10                  15
Val Ala Pro Met Ala Phe Ala
            20

<210> SEQ ID NO 12
<211> LENGTH: 31
<212> TYPE: PRT
<213> ORGANISM: Brevibacillus brevis

<400> SEQUENCE: 12

Met Lys Lys Arg Arg Val Val Asn Asn Ser Val Leu Leu Leu Leu Leu
1               5                   10                  15
Leu Ala Ser Ala Leu Ala Leu Thr Val Ala Pro Met Ala Phe Ala
            20                  25                  30
```

<210> SEQ ID NO 13
<211> LENGTH: 31
<212> TYPE: DNA
<213> ORGANISM: Artificial Sequence
<220> FEATURE:
<223> OTHER INFORMATION: chemically-synthesized PCR primer

<400> SEQUENCE: 13
ggaattctga tttcactttt tgcattctac a                            31

<210> SEQ ID NO 14
<211> LENGTH: 20
<212> TYPE: DNA
<213> ORGANISM: Artificial Sequence
<220> FEATURE:
<223> OTHER INFORMATION: chemically-synthesized PCR primer

<400> SEQUENCE: 14
agtgcactcg cacttactgt                                         20

<210> SEQ ID NO 15
<211> LENGTH: 361
<212> TYPE: DNA
<213> ORGANISM: Artificial Sequence
<220> FEATURE:
<223> OTHER INFORMATION: synthetic DNA containing MWP P2 promoter

<400> SEQUENCE: 15
ggtaccaatt ggcgccgcaa cttttgattc gctcaggcgt ttaataggat gtaattgtga    60
gcggataaca attattctgc atggctttcc tgcgaaagga ggtgcaccgc gcttgcagga   120
ttcgggcttt aaaagaaag atagattaac aacaaatatt ccccaagaac aatttgttta    180
tactggagga ggagaacaca aggtcatgaa aaaagaagg gtcgttaaca gtgtattgct    240
tctgctactg ctagctagtg cactcgcact tactgttgct cccatggctt tcgctgcagg   300
atccgtcgac tctagactcg aggaattcgg taccccgggt tcgaaatcga taagcttctg   360
t                                                                  361

<210> SEQ ID NO 16
<211> LENGTH: 44
<212> TYPE: DNA
<213> ORGANISM: Artificial Sequence
<220> FEATURE:
<223> OTHER INFORMATION: chemically-synthesized PCR primer

<400> SEQUENCE: 16
ttgctcccat ggctttcgct gcgcaacacg atgaagctca acaa               44

<210> SEQ ID NO 17
<211> LENGTH: 60
<212> TYPE: DNA
<213> ORGANISM: Artificial Sequence
<220> FEATURE:
<223> OTHER INFORMATION: chemically-synthesized PCR primer

<400> SEQUENCE: 17
cgggatccct attttggtgc ttgagcatcg tttagctttt tagcttctgc taaaattttc   60

<210> SEQ ID NO 18
<211> LENGTH: 1230
<212> TYPE: DNA
<213> ORGANISM: Brevibacillus brevis
<220> FEATURE:

```
<221> NAME/KEY: CDS
<222> LOCATION: (206)..(1171)
<220> FEATURE:
<221> NAME/KEY: RBS
<222> LOCATION: (186)..(196)
<220> FEATURE:
<221> NAME/KEY: RBS
<222> LOCATION: (94)..(103)
<220> FEATURE:
<221> NAME/KEY: sig_peptide
<222> LOCATION: (206)..(295)
<220> FEATURE:
<221> NAME/KEY: -10_signal
<222> LOCATION: (41)..(45)
<220> FEATURE:
<221> NAME/KEY: -35_signal
<222> LOCATION: (17)..(23)

<400> SEQUENCE: 18
```

| | |
|---|---|
| cgtaccaatt ggcgccgcaa cttttgattc gctcaggcgt ttaataggat gtaattgtga | 60 |
| gcggataaca attattctgc atggctttcc tgcgaaagga ggtgcaccgc gcttgcagga | 120 |
| ttcgggcttt aaaaagaaag atagattaac aacaaatatt ccccaagaac aatttgttta | 180 |

| tactagagga ggagaacaca aggtc atg aaa aaa aga agg gtc gtt aac agt | 232 |
|---|---|
|  Met Lys Lys Arg Arg Val Val Asn Ser | |
|  1           5 | |

| gta ttg ctt ctg cta ctg cta gct agt gca ctc gca ctt act gtt gct | 280 |
|---|---|
| Val Leu Leu Leu Leu Leu Leu Ala Ser Ala Leu Ala Leu Thr Val Ala | |
| 10              15              20              25 | |

| ccc atg gct ttc gct gcg caa cac gat gaa gct caa caa aat gct ttt | 328 |
|---|---|
| Pro Met Ala Phe Ala Ala Gln His Asp Glu Ala Gln Gln Asn Ala Phe | |
|         30              35              40 | |

| tat caa gtg tta aat atg cct aac tta aac gct gat caa cgt aat ggt | 376 |
|---|---|
| Tyr Gln Val Leu Asn Met Pro Asn Leu Asn Ala Asp Gln Arg Asn Gly | |
|     45              50              55 | |

| ttt atc caa agc ctt aaa gat gat cca agc caa agt gct aac gtt tta | 424 |
|---|---|
| Phe Ile Gln Ser Leu Lys Asp Asp Pro Ser Gln Ser Ala Asn Val Leu | |
| 60              65              70 | |

| ggt gaa gct caa aaa ctt aat gac tct caa gct cca aaa gct gat gcg | 472 |
|---|---|
| Gly Glu Ala Gln Lys Leu Asn Asp Ser Gln Ala Pro Lys Ala Asp Ala | |
| 75              80              85 | |

| caa caa aat aag ttc aac aaa gat caa caa agc gcc ttc tat gaa atc | 520 |
|---|---|
| Gln Gln Asn Lys Phe Asn Lys Asp Gln Gln Ser Ala Phe Tyr Glu Ile | |
| 90              95              100             105 | |

| ttg aac atg cct aac tta aac gaa gag caa cgc aat ggt ttc att caa | 568 |
|---|---|
| Leu Asn Met Pro Asn Leu Asn Glu Glu Gln Arg Asn Gly Phe Ile Gln | |
|         110             115             120 | |

| agt ctt aaa gac gat cca agc caa agc act aac gtt tta ggt gaa gct | 616 |
|---|---|
| Ser Leu Lys Asp Asp Pro Ser Gln Ser Thr Asn Val Leu Gly Glu Ala | |
|     125             130             135 | |

| aaa aaa tta aac gaa tct caa gca ccg aaa gct gac aac aat ttc aac | 664 |
|---|---|
| Lys Lys Leu Asn Glu Ser Gln Ala Pro Lys Ala Asp Asn Asn Phe Asn | |
| 140             145             150 | |

| aaa gaa caa caa aat gct ttc tat gaa atc ttg aac atg cct aac ttg | 712 |
|---|---|
| Lys Glu Gln Gln Asn Ala Phe Tyr Glu Ile Leu Asn Met Pro Asn Leu | |
| 155             160             165 | |

| aac gaa gaa caa cgc aat ggt ttc atc caa agc tta aaa gat gac cca | 760 |
|---|---|
| Asn Glu Glu Gln Arg Asn Gly Phe Ile Gln Ser Leu Lys Asp Asp Pro | |
| 170             175             180             185 | |

| agt caa agt gct aac ctt tta gca gaa gct aaa aag tta aat gaa tct | 808 |
|---|---|
| Ser Gln Ser Ala Asn Leu Leu Ala Glu Ala Lys Lys Leu Asn Glu Ser | |
|         190             195             200 | |

| caa gca ccg aaa gct gat aac aaa ttc aac aaa gaa caa caa aat gct | 856 |

-continued

| | | | | | | | | | | | | | | | |
|---|---|---|---|---|---|---|---|---|---|---|---|---|---|---|---|
| Gln | Ala | Pro | Lys 205 | Ala | Asp | Asn | Lys 210 | Phe | Asn | Lys | Glu 215 | Gln | Gln | Asn | Ala |

```
ttc tat gaa atc tta cat tta cct aac tta aat gaa gaa caa cgc aat      904
Phe Tyr Glu Ile Leu His Leu Pro Asn Leu Asn Glu Glu Gln Arg Asn
        220                 225                 230 ggt ttc atc caa agc tta aaa gat gac cca agc caa agc gct aac ctt      952
Gly Phe Ile Gln Ser Leu Lys Asp Asp Pro Ser Gln Ser Ala Asn Leu
    235                 240                 245 tta gca gaa gct aaa aag cta aat gat gca caa gca cca aaa gct gac     1000
Leu Ala Glu Ala Lys Lys Leu Asn Asp Ala Gln Ala Pro Lys Ala Asp
250                 255                 260                 265 aac aaa ttc aac aaa gaa caa caa aat gct ttc tat gaa att tta cat     1048
Asn Lys Phe Asn Lys Glu Gln Gln Asn Ala Phe Tyr Glu Ile Leu His
        270                 275                 280 tta cct aac tta act gaa gaa caa cgt aac ggc ttc atc caa agc ctt     1096
Leu Pro Asn Leu Thr Glu Glu Gln Arg Asn Gly Phe Ile Gln Ser Leu
    285                 290                 295 aaa gac gat cct tca gtg agc aaa gaa att tta gca gaa gct aaa aag     1144
Lys Asp Asp Pro Ser Val Ser Lys Glu Ile Leu Ala Glu Ala Lys Lys
300                 305                 310 cta aac gat gct caa gca cca aaa tag ggatccgtcg actctagact           1191
Leu Asn Asp Ala Gln Ala Pro Lys
    315                 320 cgaggaattc ggtaccccgg gttcgaaatc gataagctt                           1230
```

<210> SEQ ID NO 19
<211> LENGTH: 321
<212> TYPE: PRT
<213> ORGANISM: Brevibacillus brevis

<400> SEQUENCE: 19

| | | | | | | | | | | | | | | | |
|---|---|---|---|---|---|---|---|---|---|---|---|---|---|---|---|
| Met 1 | Lys | Lys | Arg | Arg 5 | Val | Val | Asn | Ser | Val 10 | Leu | Leu | Leu | Leu | Leu 15 | Leu |
| Ala | Ser | Ala | Leu 20 | Ala | Leu | Thr | Val | Ala 25 | Pro | Met | Ala | Phe | Ala 30 | Ala | Gln |
| His | Asp | Glu 35 | Ala | Gln | Gln | Asn | Ala 40 | Phe | Tyr | Gln | Val | Leu 45 | Asn | Met | Pro |
| Asn | Leu 50 | Asn | Ala | Asp | Gln | Arg 55 | Asn | Gly | Phe | Ile | Gln 60 | Ser | Leu | Lys | Asp |
| Asp 65 | Pro | Ser | Gln | Ser | Ala 70 | Asn | Val | Leu | Gly | Glu 75 | Ala | Gln | Lys | Leu | Asn 80 |
| Asp | Ser | Gln | Ala | Pro 85 | Lys | Ala | Asp | Ala | Gln 90 | Gln | Asn | Lys | Phe | Asn 95 | Lys |
| Asp | Gln | Gln | Ser 100 | Ala | Phe | Tyr | Glu | Ile 105 | Leu | Asn | Met | Pro | Asn 110 | Leu | Asn |
| Glu | Glu | Gln 115 | Arg | Asn | Gly | Phe | Ile 120 | Gln | Ser | Leu | Lys | Asp 125 | Asp | Pro | Ser |
| Gln | Ser 130 | Thr | Asn | Val | Leu | Gly 135 | Glu | Ala | Lys | Lys | Leu 140 | Asn | Glu | Ser | Gln |
| Ala 145 | Pro | Lys | Ala | Asp | Asn 150 | Asn | Phe | Asn | Lys | Glu 155 | Gln | Gln | Asn | Ala | Phe 160 |
| Tyr | Glu | Ile | Leu | Asn 165 | Met | Pro | Asn | Leu | Asn 170 | Glu | Glu | Gln | Arg | Asn 175 | Gly |
| Phe | Ile | Gln | Ser 180 | Leu | Lys | Asp | Asp | Pro 185 | Ser | Gln | Ser | Ala | Asn 190 | Leu | Leu |
| Ala | Glu | Ala 195 | Lys | Lys | Leu | Asn | Glu 200 | Ser | Gln | Ala | Pro | Lys 205 | Ala | Asp | Asn |

```
Lys Phe Asn Lys Glu Gln Gln Asn Ala Phe Tyr Glu Ile Leu His Leu
    210                 215                 220

Pro Asn Leu Asn Glu Glu Gln Arg Asn Gly Phe Ile Gln Ser Leu Lys
225                 230                 235                 240

Asp Asp Pro Ser Gln Ser Ala Asn Leu Leu Ala Glu Ala Lys Lys Leu
                245                 250                 255

Asn Asp Ala Gln Ala Pro Lys Ala Asp Asn Lys Phe Asn Lys Glu Gln
            260                 265                 270

Gln Asn Ala Phe Tyr Glu Ile Leu His Leu Pro Asn Leu Thr Glu Glu
        275                 280                 285

Gln Arg Asn Gly Phe Ile Gln Ser Leu Lys Asp Asp Pro Ser Val Ser
    290                 295                 300

Lys Glu Ile Leu Ala Glu Ala Lys Lys Leu Asn Asp Ala Gln Ala Pro
305                 310                 315                 320

Lys
```